(12) United States Patent
Meng et al.

(10) Patent No.: US 9,221,781 B2
(45) Date of Patent: Dec. 29, 2015

(54) SYNTHESIS OF POLYHYDROXY CHROMENONE COMPOUNDS AND THEIR ANTI-TUMOR EFFECTS

(71) Applicant: BEIJING SHENOGEN PHARMA GROUP LTD., Beijing (CN)

(72) Inventors: Kun Meng, Beijing (CN); Hongxia Ding, Beijing (CN); Jin Li, Beijing (CN)

(73) Assignee: BEIJING SHENOGEN PHARAM GROUP LTD., Beijing (CN)

( * ) Notice: Subject to any disclaimer, the term of this patent is extended or adjusted under 35 U.S.C. 154(b) by 0 days.

(21) Appl. No.: 14/371,866

(22) PCT Filed: Dec. 31, 2012

(86) PCT No.: PCT/CN2012/088016
§ 371 (c)(1),
(2) Date: Jul. 11, 2014

(87) PCT Pub. No.: WO2013/104263
PCT Pub. Date: Jul. 18, 2013

(65) Prior Publication Data
US 2015/0011618 A1  Jan. 8, 2015

(30) Foreign Application Priority Data

Jan. 13, 2012 (CN) .......................... 2012 1 0011031
Dec. 25, 2012 (CN) .......................... 2012 1 0573072

(51) Int. Cl.
*C07D 311/28* (2006.01)
*C07D 311/30* (2006.01)

(52) U.S. Cl.
CPC .................................... *C07D 311/30* (2013.01)

(58) Field of Classification Search
CPC .................................................. C07D 311/28
See application file for complete search history.

(56) References Cited

U.S. PATENT DOCUMENTS

| | | |
|---|---|---|
| 2010/0016352 A1 | 1/2010 | Li et al. |
| 2013/0303544 A1 | 11/2013 | Ding et al. |

FOREIGN PATENT DOCUMENTS

| | | |
|---|---|---|
| CN | 1786864 A | 6/2006 |
| CN | 101104611 A | 1/2008 |
| CN | 102018698 A | 4/2011 |
| JP | 2007332695 A | 12/2007 |
| WO | WO 2008/100977 A2 | 8/2008 |
| WO | WO 2011/047595 A1 | 4/2011 |

OTHER PUBLICATIONS

Ferrell et al. (Molecular Pharmacology (1979), 16(2), 556-68).*
Jain et al. (Indian Journal of Chemistry, Section B: Organic Chemistry Including Medicinal Chemistry (1984), 23B(10), 1002-4). Abstract.*
Deng et al. (Liebigs Annalen/Recueil (1997), (10), 2169-2175).*
Boumendjel et al. (Bioorganic & Medicinal Chemistry Letters (2000), Volume Date 2001, 11(1),75-77).*
Lee et al. (Bioorganic & Medicinal Chemistry Letters (2010), 20(19, 5709-5712).*
Wang, Z. et al., "Identification, cloning, and expression of human estrogen receptor-α36, a novel variant of human estrogen receptor-α66" Biochemical and Biophysical Research Communications (Nov. 4, 2005) pp. 1023-1027, vol. 336, No. 4.
Flouriot, G. et al., "Identification of a new isoform of the human estrogen receptor-alpha (hER-alpha) that is encoded by distinct transcripts and that is able to repress hER-alpha activation function 1" EMBO, J. (Sep. 1, 2000) pp. 4688-4700, vol. 19, No. 17.
Li, L. et al., "Plasma membrane localization and function of the estrogen receptor α variant (ER46) in human endothelial cells" Proc. Natl. Acad. Sci., USA (2003) pp. 4807-4812, vol. 100, No. 8.
Wang, Z. et al., "A variant of estrogen receptor-{alpha}, hER-{alpha}36: Transduction of estrogen- and antiestrogen—dependent membrane-initiated mitogenic signaling" Proc. Natl. Acad. Sci. USA (2006) pp. 9063-9068, vol. 103, No. 24.
Berger, S.M. et al., "Pharmaceutical salts" J. Pharm. Sci. (Jan. 1977) pp. 1-19, vol. 66, No. 1.
Lacroix, M. et al., "Relevance of Breast Cancer Cell Lines as Models for Breast Tumours: An Update" Breast Cancer Research and Treatment (Feb. 2004) pp. 249-289, vol. 83, No. 3.
International Search Report dated Apr. 9, 2009 issued in International Application No. PCT/CN2008/073806.
Cerqueira F. et al., "Inhibition of Lymphocyte Proliferation by Prenylated Flavones: Artelastin as a Potent Inhibitor", Life Sciences 73:2321-2334 (2003).
Jain A.C. et al., "Constitution and Synthesis of Naturally Occurring Isopentenylated Kaempferol Derivatives, Noranhydroicaritin and Isoanhydroicaritin and Related Flavonols Including Di-O-Methylicaritin", Aust. J. Chem. 28:607-619 (1975).
Jain A.C. et al., "Synthesis of Sericetin and Related Compounds", Current Science 42(9):314-315 (May 5, 1973).
Extended European Search Report dated Jun. 9, 2015 received from Application No. 12864757.5.

* cited by examiner

*Primary Examiner* — Bruck Kifle
(74) *Attorney, Agent, or Firm* — Scully, Scott, Murphy & Presser, P.C.

(57) ABSTRACT

The present invention is directed to chromenone compounds of formula (I), pharmaceutically acceptable salts, prodrugs thereof, and the composition comprising the compounds or the like. They can be used to modulating the function of estrogen receptor ER-α36 preventing and/or treating the estrogen related diseases, such as breast cancer, leukemia, liver cancer and etc.

8 Claims, 11 Drawing Sheets

SYNTHESIS OF POLYHYDROXY CHROMENONE COMPOUNDS AND THEIR ANTI-TUMOR EFFECTS

FIELD OF THE INVENTION

The present invention is directed to compounds of polyhydroxy chromenone, pharmaceutically accepted salts, prodrugs thereof, and a pharmaceutical composition comprising the compounds or the like. The present invention is also directed to the use of the compounds, pharmaceutically accepted salts, prodrugs thereof, and a pharmaceutical composition in preparation of a medication for prevention and/or treatment of diseases related to tumor.

STATE OF THE ART

Estrogens are a group of hormones that are involved in many critical physiological functions in human body. Estrogen functions include promoting development of female sex organs, fully preparing the breast and uterus for pregnancy and breast feeding after childbirth. Estrogens also play important roles in maintaining proper cardiovascular functions and bone density. It is well known that estrogens can stimulate cell proliferation and may increase the risk of women suffering from cancer, especially breast cancer and uterus cancer.

Estrogens bind to estrogen receptors in target cells to regulate cell functions. Two types of estrogen receptors are discovered in human cells (ERs), ER-α and ER-β. They have a similar protein structure, each has three separate but interacting functional domains: N-terminal domain (A/B domain), central DNA-binding domain (C domain), and C-terminal ligand-binding domain (D/E/F domain). The N-terminal domain has ligand-independent activation function (AF-1), which is involved in interaction with co-activators and transcriptional activation of target genes in absence of ligands. The DNA binding-domain plays an important role in receptor dimerization and binding special DNA sequence. The C-terminal ligand binding domain mediates ligand binding and has a ligand-dependent transactivation function (AF-2), for activating gene transcription in presence of ligands.

The full-length ER-α is identified as a 66kDa protein and referred as ER-α66. ER-α66 contains all three function domains. A splice variant of ER-α66 was subsequently discovered and named ER-α46. ER-α46 has a molecular weight of about 46 KDa and lacks the N-terminal AF-1 domain of ER-α66. Recently, a novel 36 kDa ERα variant, ER-α36, is identified. It lacks the N-terminal AF-1 domain and the C-terminal AF-2 domain of ER-α66 (Wang et al., Biochem. Biophys. Res.Commun. 336, 1023-1027 (2005)).

ER-α66 is well believed to mediate estrogen-stimulated cell proliferation via transcriptional activation of its target genes. Binding of estrogen to ER-α66 activates the transactivation domain of ER-α66 and thus stimulates expression of downstream target genes and eventually leads to cell proliferation. ER-α46 is found to mediate membrane-initiated and estrogen-stimulated rapid NO synthesis (Li et al., Proc. Natl. Acad. Sci., USA 100: 4807-4812 (2003)). It is also shown that ER-α46, which lacks the AF-1 domain, inhibits the AF-1 activity of ER-α66 (Flouriot, G., EMBO, 19, 4688-4700, (2000)). Since ER-α36 lacks both AF-1 and AF-2 transcriptional activation domains, it functions as a dominant-negative inhibitor to inhibit both AF-1 and AF-2 functions of ER-α and ER-β. In addition, ER-α36 is localized primarily on plasma membrane and mediates membrane-initiated mitogenic estrogen signaling that stimulates cell proliferation. (Wang et al., Biochem. Biophys. Res.Commun. 336, 1023-1027 (2005); Wang et al., Proc.Natl.Acad.Sci., USA 103: 9063-9068 (2006)).

Extensive studies have shown that estrogen signaling is mediated via classic nuclear transcriptional activation pathways as well as non-classic membrane-initiated signaling pathways. It seems that both ER-α66 and ER-α46 function primarily in the nucleus while ER-α36 functions mainly through outside of the nucleus.

It is also shown that ER-α36 lacks helix 8-12 of the ligand-binding domain of the original ER-α66, which totally changes ligand binding specificity of ER-α36. Thus, ER-α36 may bind to different ligands from those bound to ER-α66 and ER-β.

As diseases related to estrogen receptor continue to affect many individuals, there remains an urgent need to discover novel compounds and methods useful to prevent and/or treat such diseases.

SUMMARY OF THE INVENTION

The present invention provides chromenone compounds shown as formula (I), Pharmaceutically acceptable salt or prodrug thereof for modulating new estrogen receptor ER-α36 and a pharmaceutical composition comprising the compounds or the like.

Please amend page 3, third paragraph under Formula (I) of the specification as follows:
when $R^1$ is methyl, and $R^3$ and $R^5$ are hydrogen, then $R^4$ is not chlorine.

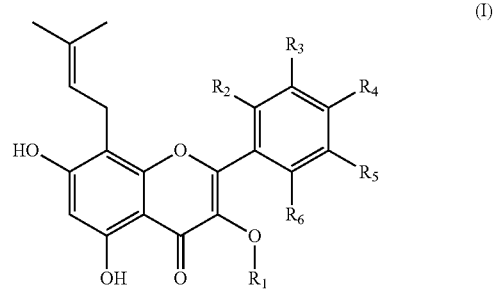

(I)

Wherein:
$R^1$ is selected from the group consisting of hydrogen, $(C_{1-6})$ alkyl, and $(C_{1-6})$ alkyl substituted with one or more halogen atoms;
$R^2$, $R^3$, $R^4$, $R^5$ and $R^6$ are independently selected from the group consisting of hydrogen, $(C_{1-4})$ alkyl, $(C_{1-4})$ alkyl substituted with one or more halogen atoms, halogen, cyano, $(C_1-C_4)$ alkoxy substituted with one or more halogen atoms; and $R^2$, $R^3$, $R^4$, $R^5$ and $R^6$ are not simultaneously hydrogen;
when $R^1$ is methyl and $R^3$ and $R^5$ are hydrogen, then $R^4$ is not chloride.

DETAILED DESCRIPTION OF THE INVENTION

Compound and Derivatives

Figure 1:
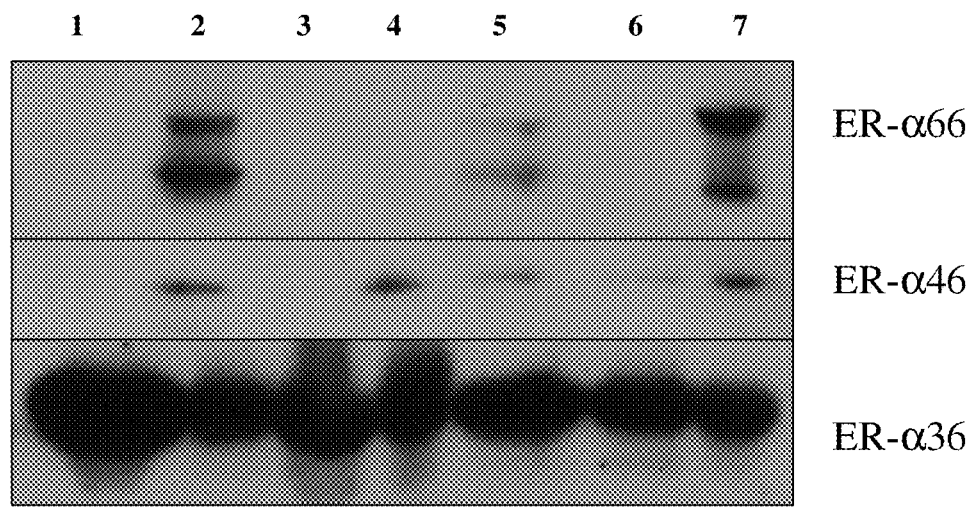
FIG. 1 shows Western blot results depicting the expression of ER-α66, ER-α46 and ER-α36 in human breast cancer samples. Lane 1: normal breast tissue; Lane 2: infiltrating ductal carcinoma; Lane 3: infiltrating ductal carcinoma; Lane 4: invasive ductal carcinoma; Lane 5: infiltrating lobular carcinoma; Lane 6: infiltrating lobular carcinoma; Lane 7: non-invasive ductal carcinoma.

In some embodiments of the present invention, the chromenone compounds, pharmaceutically acceptable salts, prodrugs thereof and the pharmaceutical composition comprising the compound or the like are provided. They can function to regulate the estrogen receptor ER-α36, prevent and/or treat the disease mediated by ER-α36 receptor, such as cancer, etc.

In some embodiments, the present invention provides the compound of formula (I), the pharmaceutically acceptable salts, prodrugs thereof, and the pharmaceutical composition comprising the compound or the like, wherein:

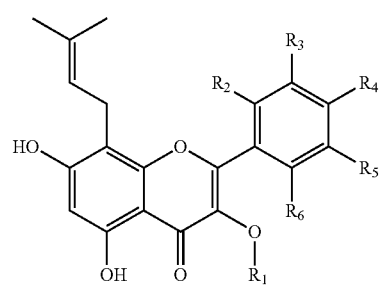

(I)

$R^1$ is selected from the group consisting of hydrogen, $(C_{1-6})$ alkyl, and $(C_{1-6})$ alkyl substituted with one or more halogen atoms;

$R^2$, $R^3$, $R^4$, $R^5$ and $R^6$ are independently selected from the group consisting of hydrogen, $(C_{1-4})$ alkyl, $(C_{1-4})$ alkyl substituted with one or more halogen atoms, halogen, cyano, and $(C_1-C_4)$ alkoxy substituted with one or more halogen atoms; and $R^2$, $R^3$, $R^4$, $R^5$ and $R^6$ are not simultaneously hydrogen;

When $R^1$ is methyl and $R^3$ and $R^5$ are hydrogen, then $R^4$ is not chlorine.

In a certain embodiment, the compound of formula (I) comprises the compound of formula (II) which has following structure:

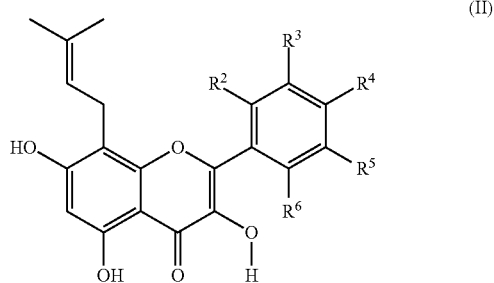

(II)

Wherein:

$R^2$, $R^3$, $R^4$, $R^5$ and $R^6$ are independently selected from the group consisting of hydrogen, $(C_{1-4})$ alkyl, $(C_{1-4})$ alkyl substituted with one or more halogen atoms, halogen, cyano, and $(C_{1-4})$ alkoxy substituted with one or more halogen atoms; and $R^2$, $R^3$, $R^4$, $R^5$ and $R^6$ are not simultaneously hydrogen.

In a certain embodiment, the compound of formula (I) comprises the compound of formula (III) which has following structure:

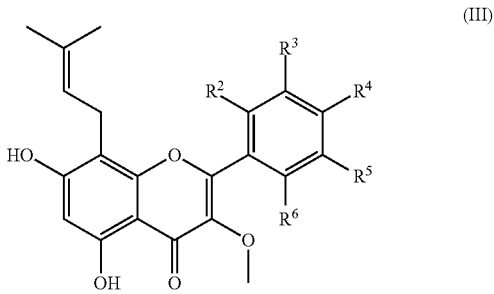

(III)

Wherein, $R^2$, $R^3$, $R^4$, $R^5$ and $R^6$ are independently selected from the group consisting of hydrogen, $(C_1-C_4)$ alkyl, $(C_1-C_4)$ alkyl substituted with one or more halogen atoms, halogen, cyano, and $(C_{1-4})$ alkoxy substituted with one or more halogen atoms, and $R^2$, $R^3$, $R^4$, $R^5$ and $R^6$ are not simultaneously hydrogen, and when $R^3$ and $R^5$ are hydrogen, $R^4$ is not chlorine.

The especially preferred compounds of formula (I) are comprising but not limited to the following compounds:

2-(4-trifluoromethylphenyl)-3,5,7-trihydroxy-8-(3-methyl-2-buten-1-yl)-4H-chromen-4-one;
2-(4-fluorophenyl)-3,5,7-trihydroxy-8-(3-methyl-2-buten-1-yl)-4H-chromen-4-one;
2-(3-fluoro-4-chlorophenyl)-3,5,7-trihydroxy-8-(3-methyl-2-buten-1-yl)-4H-chromen-4-one;
2-(4-chlorophenyl)-3,5,7-trihydroxy-8-(3-methyl-2-buten-1-yl)-4H-chromen-4-one;
2-(4-trifluoromethoxyphenyl)-3,5,7-trihydroxy-8-(3-methyl-2-buten-1-yl)-4H-chromen-4-one;
2-(3,4-dichlorophenyl)-3,5,7-trihydroxy-8-(3-methyl-2-buten-1-yl)-4H-chromen -4-one;
2-(3-trifluoromethyl-4-cholophenyl)-3,5,7-trihydroxy-8-(3-methyl-2-buten-1-yl )-4H-chromen-4-one;
2-(4-bromophenyl)-3,5,7-trihydroxy-8-(3-methyl-2-buten-1-yl)-4H-chromen-4-one;
2-(3,4-difluorophenyl)-3-methoxy-5,7-dihydroxy-8-(3-methyl-2-buten-1-yl)-4H-chromen-4-one;
2-(4-trifluoromethylphenyl)-3-methoxy-5,7-dihydroxy-8-(3-methyl-2-buten-1-yl)-4H-chromen-4-one;
2-(4-trifluoromethoxyphenyl)-3-methoxy-5,7-dihydroxy-8-(3-methyl-2-buten-1-yl)-4H-chromen-4-one;
2-(3-trifluoromethyl-4-chlorophenyl)-3-methoxy-5,7-dihydroxy-8-(3-methyl-2-buten-1-yl)-4H-chromen-4-one;
2-(4-bromophenyl)-3-methoxy-5,7-dihydroxy-8-(3-methyl-2-buten-1-yl)-4H-chromen -4-one;

A compound of formula

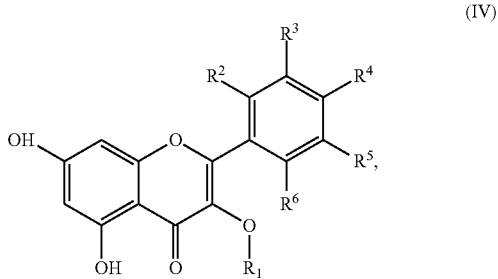

(IV)

Wherein:

$R^1$ is selected from the group consisting of hydrogen, $(C_{1-6})$ alkyl, and $(C_{1-6})$ alkyl substituted with one or more halogen atoms;

$R^2$, $R^3$, $R^4$, $R^5$ and $R^6$ are independently selected from the group consisting of hydrogen, $(C_{1-4})$ alkyl, $(C_{1-4})$ alkyl substituted with one or more halogen atoms, halogen, cyano and $(C_{1-4})$ alkoxy substituted with one or more halogen atoms, and $R^2$, $R^3$, $R^4$, $R^5$ and $R^6$ are not simultaneously hydrogen;

When $R^1$ is methyl and $R^3$ and $R^5$ are hydrogen, then $R^4$ is not chloride.

The compound (IV) is an intermediate of compound (I).

The compounds and the derivates thereof in the present invention are named in accordance with IUPAC (International Union of Pure and Applied Chemistry) Naming System or CAS (Chemical Abstract Service, Columbus, Ohio) Naming System.

The followings are the definition of the terms used in the present invention. Unless indicated otherwise, the primary definitions of the groups or the terms comprising an independent group or a part of other groups are applicable to the whole description.

The term "substituted" means that a hydrogen atom of a molecule has been replaced with a different atom or molecule. The atom or molecule which replaces the hydrogen atom is denoted as a "substituent".

The minimum and maximum value of carbon atom number of the $C_nH_n$— is denoted with the prefix, such as, the prefix of $(C_a-C_b)$ alkyl means any alkyl comprising the carbon atoms number from "a" to "b". Thus, such as $(C_1-C_6)$ alkyl means the alkyl comprising carbon atoms from 1 to 6.

The term "alkoxy" means the linear or branched monovalent saturated fatty chain group bonded with an oxygen atom at one end, including but not limited methoxy, ethoxy, propoxy, butoxy, iso-butoxy, tert-butoxy or the like.

The term "alkyl" means straight or branched, monovalent, saturated fatty chain, comprising but not limited to the group such as methyl, ethyl, propyl, isopropyl, butyl, isobutyl, pentyl, iso-pentyl, hexyl or the like.

The term "halogen" or "halogen atom" means the atom of chlorine, bromine, fluorine and iodine or the corresponding group.

The term "heteroaryl" means aromatic group of monocycle or polycycle wherein one or more carbon atoms is/are replaced by one or more heteroatoms such as nitrogen, oxygen or sulfur. Examples of heterocycloalkyl rings include but not limited to benzofuranyl, benzothiophenyl, benzimidazolyl, benzoxazolyl, benzothiazolyl, benzopyranyl, furyl, imidazolyl, indazolyl, indolizinyl, indolyl, isobenzofuryl, isoindolyl, isoquinolyl, isothiazole, isoxazole, naphthyridinyl, oxadizolyl, oxazinyl, oxazolyl, phthalazinyl, pteridinyl, guaninyl, pyranyl, pyrazinyl, pyrazolyl, pyridazinyl, pyrido [3,4-b] indolyl, pyridinyl, pyrimidinyl, pyrrolidinyl, quinolizyl, quinolinyl, quinoxalinyl, thiadizolyl, thiatrizolyl, thiazolyl, thienyl, triazinyl, triazolyl, xanthenyl or the like.

The term "-oxo" means a carbonyl group formed by the combination of a carbon atom (s) and oxygen atom (s).

The prodrugs, solvates of the compounds of the present invention are also in consideration. The term "prodrug" refers to a compound that is a drug precursor which, following administration to a subject, releases the active drug in vivo via a chemical or metabolism process (e.g., upon being brought to physiological pH or through enzyme activity). A discussion of the synthesis and use of the prodrug can be found in "*Prodrugs* as Novel Delivery Systems," vol. 14 of the ACS Symposium Series, and in Bioreversible Carriers in Drug Design, ed. Edward B. Roche, American Pharmaceutical Association and Pergamon Press, 1987, both of which are incorporated herein by reference. The term "prodrug" may include a metabolic precursor of a compound of the present invention. The prodrug may be inactive when administered to a subject but can be converted in vivo to a compound of formula (I) of the invention. The prodrug can be naturally existing compounds or synthetic compounds.

The compound of formula (I) in the present invention can be in a form of non-solvated, or solvated, such as pharmaceutically hydrated, ethanolated or the like. And it is intended that the present invention includes all of the solvates and non-solvates of the compounds. The preferred solvate of the compound of formula (I) is hydrate.

All of the stereoisomeric of the compounds, such as possible stereoisomeric from asymmetric carbon atom of the R substituent group of formula (I) including enantiomer and diastereomer are within the scope of the present invention. The stereoisomeric and the mixture of the compounds shown in formula (I) including racemic mixture are also a part of the present invention. Further, all of the geometric isomers and positional isomers, such as, if the compound of formula (I) has a double bond, the cis- and trans- and the mixture thereof are all within the scope of the present invention.

Diastereomeric mixtures can be separated into their individual diastereomers on the basis of their physical chemical differences by methods well-known to those of ordinary skill in the art, such as by chromatography and/or fractional crystallization. Enantiomers can be separated by converting the enantiomeric mixture into a diasteriomeric mixture by reaction with an appropriate optically active compound, then separating the diastereomers and converting (e.g., hydrolyzing) the diastereomers to the corresponding pure enantiomers. Also, some of the compounds of formula (I) may be altropisomers (e.g., substituted biaryls), which are also considered as a part of the invention.

The phrase "pharmaceutically acceptable" indicates that the designated carrier, vehicle, diluents, excipient (s), and/or salt are/is generally chemically and/or physically compatible with the other ingredients comprising the formulation and physiologically compatible with the recipient thereof The term "salts" and "pharmaceutically acceptable salts" refer to acid salt and/or basic salt formed by compounds of formula (I) or stereoisomer thereof and inorganic and/or organic acid and base. The salts and pharmaceutically acceptable salts also comprise amphoteric salt (intramolecular salt), and quaternary ammonium salt such as alkyl ammonium salt. The salts may be obtained directly after isolation and purification. Further, the salts may be obtained from the compounds of formula (I) or the stereoisomer, prodrug thereof mixed with appropriate acid or base (e.g. equivalent). The salts can be collected by filtering precipitate from solution or by evaporation of the solvent, or by freeze drying after reaction in the water medium.

Acid addition salts include hydrobromide, hydroiodide, hydrochloride, sulfate, hydrosulfate, nitrate, acetate (including the salts formed with acetic acid, or trichloroacetic for example, trifluoroacetic), oxalate, alginate, ascorbate, aspartate, butyrate, camphorate, camphor sulfonate, cyclopentyl propionate, digluconate, ethylene sulfonate, 2-hydroxy ethyl sulfonate, 2-naphthalene sulfonate, nicotinate, persulfate, 3-phenyl propionate, picrate, pivalate, propionate, salicylate, benzene sulfonate, palmitate, stearate, laurate, borate, benzoate, lactate, phosphate, tosylate, citrate, maleate, fumarate, succinate, tartrate, thiocyanate, naphthylate, mesylate, glucoheptonate, lactobionate, dodecyl sulfonate, adipate or the like.

Basic salts (for example: the salt formed with carboxy or phenoxy of R substituent) include ammonium, the salt of alkaline metal (such as sodium, lithium and potassium), alkaline earth metal (such as calcium and magnesium), the salt formed with organic base (such as organic amine) (including but not limited to dibenzyl ethylene amine, dicyclohexylamine, hydrabamine, N-methyl-D-glucosamine, tetrabutylamine) and the salts formed with amino acid such as arginine, lysine or the like. Further, basic salts include quaternary ammonium formed with alkali agent comprising nitrogen, and not limited to ammonium, tetramethylammonium, tetraethylammonium, methylamine, dimethylamine, trimethylamine, triethylamine, ethylamine or the like. For additional examples see, Berge, et al., J. Pharm. Sci., 66, 1-19 (1977).

It is also possible that the compounds of formula (I) may exist as tautomeric isomers in equilibrium, and all such forms are embraced within the scope of the invention.

In an embodiment, isotopically-labeled compounds of formula (I), which is identical to those recited herein, but for the fact that one or more atoms is/are replaced by an another atom having an atomic mass or mass number different from that commonly existing in nature are provided in the present invention. Examples of isotopes that can be incorporated into compounds of formula (I) include isotopes of hydrogen, carbon, nitrogen, oxygen, phosphorus, fluorine and chlorine, such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$. The compounds of formula (I) comprising the above isotopes and/or that of other atoms, the stereoisomers and prodrugs thereof, and the pharmaceutically acceptable salts of the compounds, stereoisomers, or prodrugs are intended to be within the scope of the present invention.

Certain isotopically-labeled compounds of formula (I), for example those compounds labeled with $^3H$ and $^{14}C$ or the like can be used in compound and/or substrate tissue distribution assays. Because the tritium (i.e. $^3H$) isotopes and carbon14 (i.e. $^{14}C$) isotopes are particularly preferred for their relative ease of preparation and facile detection. Furthermore, some isotopes such as deuterium, (i.e. $^2H$) may afford certain therapeutic advantages resulting from greater metabolic stability, (for example, increased half-life in vivo, or reduced dosage requirements) and hence, may be preferred in some circumstances. The isotopically-labeled compounds of formula (I) can generally be prepared by methods known to one of ordinary skill in the art, such as by substituting an isotopically-labeled reagent for non-isotopically-labeled reagent.

Use of Invention

The compound of the present invention is a new modulator for estrogen receptor ER-α36, and can modulate the function of ER-α36 in cells in vivo and in vitro. Therefore, the compound of formula (I) of the present invention can be used for the treatment and/or prevention the diseases via ER-α36, especially related to tumor.

In certain embodiments, the method of modulating the function of ER-α36 in cells is provided. The method comprises administrating the compound of formula (I) to cells endogenously or exogenously expressing ER-α36 by gene engineering, also, to cells with or without other estrogen receptor (such as, ER-α66, ER-α46 and ER-β). In a certain embodiment, the cells endogenously express ER-α36. In a preferred embodiment, the cell is a cancer cell endogenously expressing ER-α36. The cells expressing ER-α36 are comprising but not limited to the cells of breast cancer, leukemia, liver cancer, lymphoma, lung cancer, myeloma, prostate cancer, ovarian cancer, endometrial cancer, colon cancer and gastric cancer. In a more preferred embodiment, the cells expressing ER-α36 are breast cancer, leukemia, liver cancer, lymphoma, endometrial cancer and ovarian cancer cells which endogenously express ER-α36. The breast cancer cells expressing ER-α36 comprise but not limited to the cells of MCF7, MDA-MB-231 and SKBR-3. The leukemia cells comprise but not limited to the cells of K562, MV-4-11, SUM159, HL-60 and Molt-4. The endometrial cancer cells expressing ER-α36 comprise but not limited to Hec1A cells. The liver cancer cells expressing ER-α36 comprise but not limited to A2780, BEL7402, BEL7404, HEL-9204, Hep2G, Hep3B and Primary liver cancer stem cell Hep-12 originated from patients. The lymphoma cells expressing ER-α36 comprise but not limited to Daudi. The expression of endogenous ER-α36 can be increased or decreased by the treatment of a reagent comprising serum, E2β (17β-estradiol), tamoxifen and fulvestrant. (ICI 182,780)

In another embodiment, the present invention provides a method of preparing the cells expressing exogenous ER-α36. The cells can be prepared by genic engineer known to the skill in the art (refer to Sambook etc, Molecular Cloning, A Laboratory Manual (2d Ed. 1989) (Cold Spring Harbor Laboratory)). In brief, an exogenous ER-α36 gene is prepared and inserted into an expression vector, then transfected to host cells, and then the host cells are cultured in the culture medium applicable to expressing exogenous ER-α36. The gene sequence of human ER-α36 is disclosed in Biochem. Biophys. Res. Commun. 336, 1023-1027 (2005) Wang et al. (GenBank registration No. BX640939). The cells expressing exogenous ER-α36 can express endogenous ER-α36 or not. The endogenous or exogenous expressing level of ER-α36 in cells can be increased or decreased by the treatment of a reagent comprising serum, E2β (17β-estradiol), tamoxifen and fulvestrant. (ICI 182,780).

Thereby, the compounds of formula (I) of the present invention can be used to preparation of medication for the prevention and/or treatment of the cancer related to ER-α36 comprising but not limited to anal cancer, bile duct cancer, bladder cancer, bone cancer, colorectal cancer (colon cancer, rectal cancer), brain cancer, breast cancer, the carcinoid, cervical cancer, endocrine related cancer, endometrial cancer, eye cancer, gallbladder cancer, head and neck cancer, Kaposi's sarcoma cancer, renal carcinoma, laryngeal carcinoma, leukemia, liver cancer, lung cancer, lymphoma, melanoma, mesothelioma, myeloma, neuroendocrine cancer, esophageal cancer, ovarian cancer, pancreatic cancer, penis cancer, prostate cancer, skin cancer, soft tissue sarcoma, spinal cord cancer, gastric cancer, testes cancer, thyroid cancer, vagina cancer, vulva cancer or uterus cancer. In preferred embodiment, the cancer related to ER-α36 includes breast cancer, cervical cancer, colon cancer, endometrial cancer, leukemia, liver cancer, lymphoma, lung cancer, myeloma, ovary cancer, prostate cancer, gastric cancer, pancreatic cancer, renal carcinoma, melanoma, thyroid cancer, soft tissue sarcomas cancer or uterus cancer. In more preferred embodiment, the cancer related to ER-α36 includes breast cancer, liver cancer, lymphoma, prostate cancer, gastric cancer, lung cancer, colon cancer, pancreatic cancer, endometrial cancer, ovarian cancer and leukemia.

The subject may be a mammal, such as a dog, cat, cow, sheep, horse or human, preferably a human being. The effective amount of the compounds vary according to the disease difference and is readily ascertainable by one of ordinary skill in the art having benefit of the instant disclosure.

In certain embodiments, the compounds of the invention may be used in combination with one or more other anticancer agents. Suitable anticancer agents include, but are not limited to alkylating agents, nitrogen mustards, folate antagonists, purine antagonists, pyrimidine antagonists, spindle poisons, topoisomerase inhibitors, apoptosis inducing agents, angiogenesis inhibitors, podophyllotoxins, nitrosoureas, antimetabolites, protein synthesis inhibitors, kinase inhibitors, Antiestrogens, Cisplatin, Carboplatin, Interferon, Asparginase, Leuprolide, Flutamide, Megestrol, Mitomycin, Bleomycin, Doxorubicin, Adriamycin, Iirinotecan and Taxol. In one embodiment, the anticancer agents are antiestrogens such as tamoxifen and fulvestrant (ICI182,750).

In certain embodiments of the present invention, a compound of formula (I), a stereoisomer, or prodrugs thereof, or a pharmaceutically acceptable salt of the stereoisomer, or prodrug, may be administered in the form of a pharmaceutical composition comprising a pharmaceutically acceptable carrier, vehicle, or diluent. They can be prepared to the medication for the prevention and/or treatment a subject suffering from diseases related to ER-α36.

In certain embodiments, the composition of the present invention can be used for the treatment of animal diseases. The ordinary veterinarian can administer in a form of pharmaceutically acceptable preparation of the present compounds, or veterinary acceptably salt, or veterinary acceptably solvent or the prodrug thereof. The veterinarian can determine the appropriate dosage and the method of administration to an animal.

If a combination of active compounds is used, they may be administered simultaneously, separately or sequentially.

Methods for Preparing Compounds

The compounds of formula (I) can be prepared by different synthetic methods. Typically, preparing methods is demonstrated as follows. $R^1$, $R^2$, $R^3$, $R^4$, $R^5$, $R^6$ are defined as aforesaid, unless indicated otherwise.

It is obvious to the person in the art, the detail methods of preparing compounds are slightly vary from the difference of the compounds structures. Further, it is necessary to protect unstable or active groups by the conventional protecting group (shown as P) in most preparing methods as follows. The property of the protecting groups and the methods of inducing or disposing the groups are known to the art. (examples refer to Greene T. W. "Protective Groups in Organic Synthesis", John Wiley & Sons, New York, 1991) The following schemes of 1 to 3 and the related description are as examples of preparing the compounds of formula (I), and are not intended to limit the scope of the prevent invention.

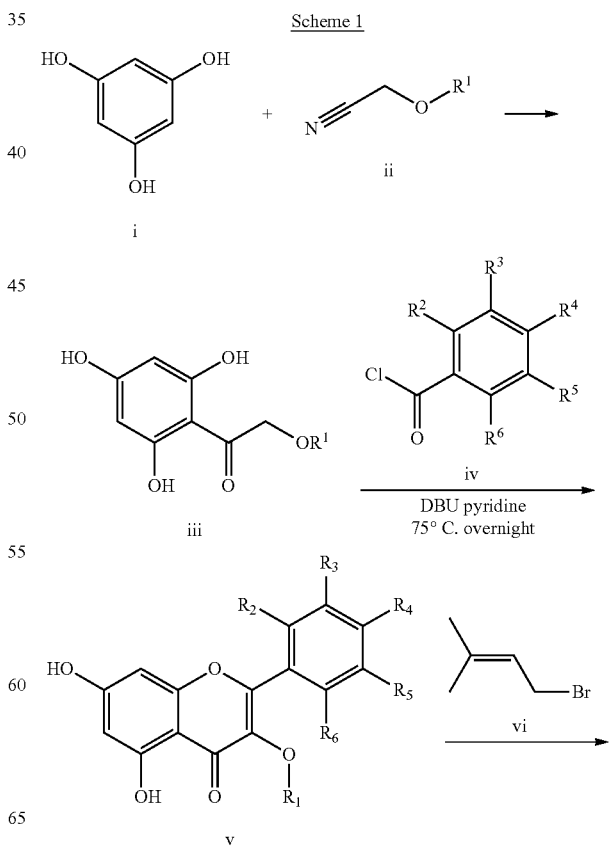

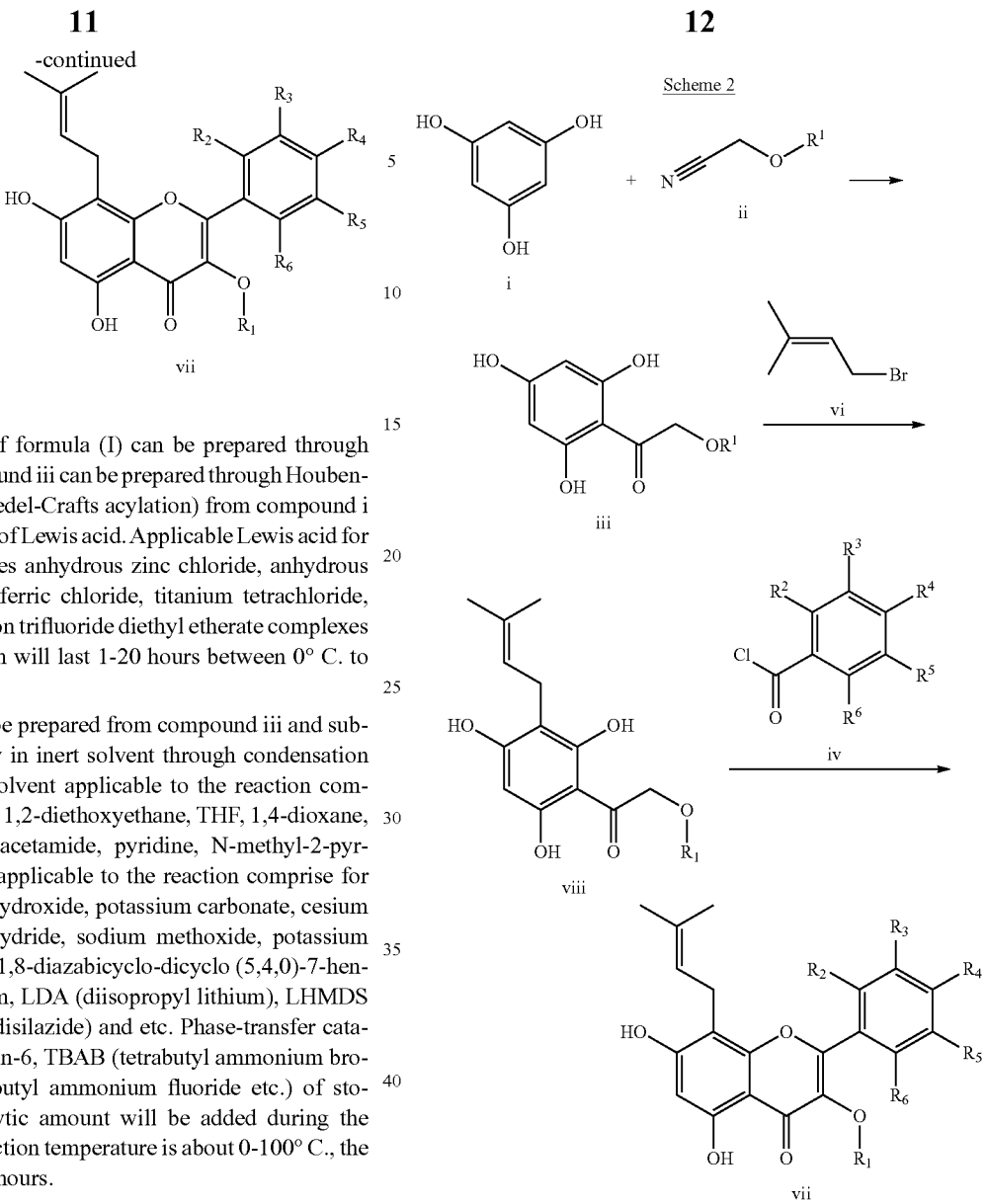

The compounds of formula (I) can be prepared through several steps. Compound iii can be prepared through Houben-Hoesch reaction (Friedel-Crafts acylation) from compound i and ii under catalysis of Lewis acid. Applicable Lewis acid for the reaction comprises anhydrous zinc chloride, anhydrous aluminum chloride, ferric chloride, titanium tetrachloride, stannic chloride, boron trifluoride diethyl etherate complexes and etc. This reaction will last 1-20 hours between 0° C. to 120° C.

Compound v can be prepared from compound iii and substituted compound iv in inert solvent through condensation reaction. The inert solvent applicable to the reaction comprises, such as DME, 1,2-diethoxyethane, THF, 1,4-dioxane, DMF, N,N-dimethylacetamide, pyridine, N-methyl-2-pyrrolidone. The alkali applicable to the reaction comprise for example potassium hydroxide, potassium carbonate, cesium carbonate, sodium hydride, sodium methoxide, potassium tert-butoxide, DBU (1,8-diazabicyclo-dicyclo (5,4,0)-7-hendecene), butyl lithium, LDA (diisopropyl lithium), LHMDS (lithium hexamethyldisilazide) and etc. Phase-transfer catalyst (such as 18-crown-6, TBAB (tetrabutyl ammonium bromide), TBAF (tetrabutyl ammonium fluoride etc.) of stoichiometric or catalytic amount will be added during the reaction. And the reaction temperature is about 0-100° C., the reaction time is 1-20hours.

The compound vii can be prepared from prenyl bromide and compound v under alkaline condition. The solvent applicable to the reaction comprises such as methanol, DMF (N,N-dimethyl acetamine), THF (tetrahydrofuran), water, toluene, DME (1,2-dimethoxy ethane), and solvent mixture, such as methanol-water, DMF-water, THF-water, and etc. The preferred solvent in the reaction is water. The alkaline applicable to the reaction comprises such as potassium hydroxide, potassium carbonate, cesium carbonate, sodium methoxide, sodium hydroxide, potassium tert-butoxide, DBU (1,8-diazabicyclo-dicyclo(5,4,0)-7-hendecene), butyl lithium, LDA (diisopropyl lithium), LHMDS (lithium hexamethyldisilazide) and etc. The reaction temperature is conventionally about 0-100° C., preferably, the reaction time is 1-20 hours.

In methods of chemical synthesis, the important two steps are respectively inducement of isopentenyl and closing parent ring of chromenone. The sequence of the two steps can be modulated according to property of different substituent groups. Therefore, the compound of the present invention can be prepared through scheme 2.

In scheme 2, the reaction condition of every type of reaction is similar to that of scheme 1. The compound viii can be prepared from compound iii and prenyl bromide under alkali condition. The solvent applicable to the reaction comprises such as methanol, DMF (N,N-dimethyl acetamine), THF (tetrahydrofuran), water, toluene, DME (1,2-dimethoxy ethane), and solvent mixture, such as methanol-water, DMF-water, THF-water, and etc. The preferred solvent in the reaction is water. The alkaline applicable to the reaction comprises such as potassium hydroxide, potassium carbonate, cesium carbonate, sodium methoxide, sodium hydroxide, potassium tert-butoxide, DBU (1,8-diazabicyclo-dicyclo(5,4,0)-7-hendecene), butyl lithium, LDA (diisopropyl lithium), LHMDS (lithium hexamethyldisilazide) and etc. The reaction temperature is conventionally about 0-100° C., preferably, the reaction time is 1-20 hours.

The compound vii can be prepared from compound viii and substituted acyl chloride iv in inert solvent through condensation reaction. The inert solvent applicable to the reaction comprises ether, such as DME, 1,2-diethoxyethane, THF, 1,4-dioxane, DMF, N,N-methylacetamide, pyridine, N-methyl-2-pyrrolidone. The reaction is applicable to alkali condition, comprising such as potassium hydroxide, potassium carbonate, cesium carbonate, sodium hydroxide, sodium methoxide, potassium tert-butoxide, DBU (1,8-diazabicyclo-dicyclo (5,4,0)-7-hendecene), butyl lithium, LDA (diisopropyl lithium), LHMDS (lithium hexamethyldisilazide) and etc. A stoichiometric or catalytic amount of phase transfer-catalyst can be added in the reaction, such as 18-cown-6, TBAB (tetrabutylammonium bromide), TBAF (tetrabutylammonium fluoride) and etc. The reaction temperature is conventionally about 0-140° C., preferably, the reaction time is 1-20 hours under solvent reflux. When $R^1$ is hydrogen, the compound of formula (I) can be prepared according to the following scheme 3.

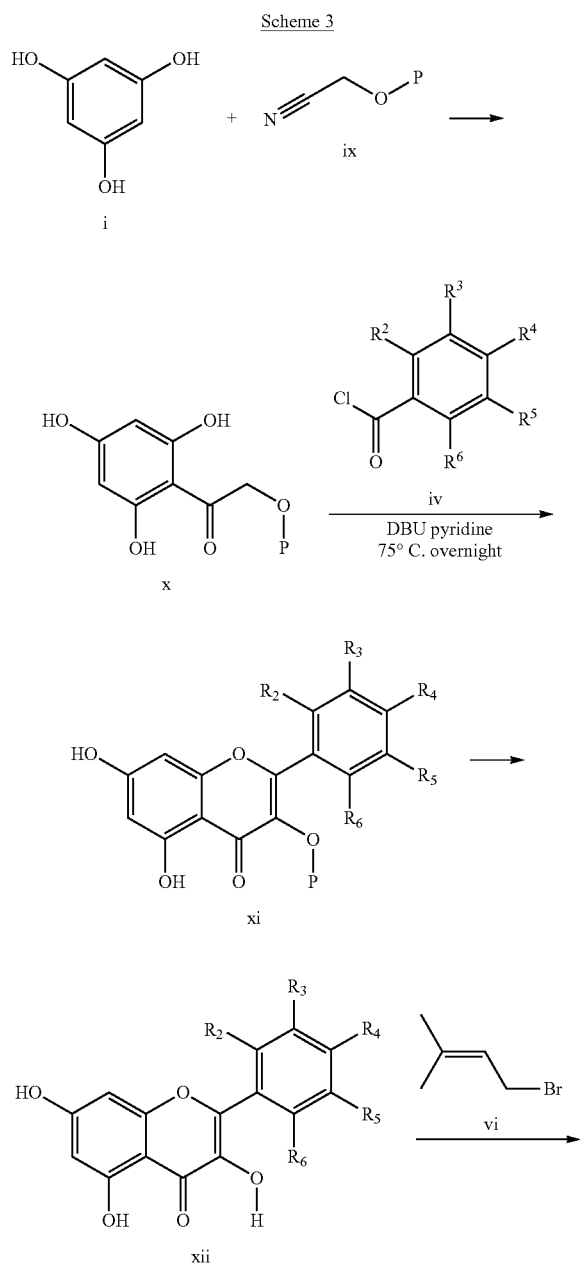

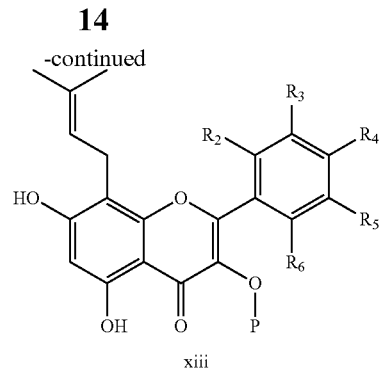

P is a protective group for hydroxy group in scheme 3. Compound xii can be prepared through removing protective group of compound xi. The removal methods vary according to different protective groups, and the methods are mainly referred to "protective groups in organic synthesis" (Greene T. W et. John Wiley & Sons, New York, 1991). The preferred protective group is selected from the group consisting of benzyl, benzoyl, Carbobenzoxy, TBDMS (tertbutyldimethylsilyl), THP (tetrahydropyrane), methyl, MOM (methoxymethyl), PMB (para-methoxybenzyl) and etc.

The compound xiii can be prepared by reaction of prenyl bromide with compound xii under alkali condition. The solvent applicable to the reaction comprises such as methanol, DMF (N,N-dimethyl acetamine), THF (tetrahydrofuran), water, toluene, DME (1,2-dimethoxy ethane), and solvent mixture such as methanol-water, DMF-water, tetrahydrofuran-water and etc. The preferred solvent is water in the reaction. Alkali applicable to the reaction comprises for example potassium hydroxide, potassium carbonate, cesium carbonate, sodium methoxide, sodium hydride, potassium tert-butoxide, DBU (1,8-diazabicyclo-dicyclo(5,4,0)-7-hendecene), butyl lithium, LDA (diisopropyl lithium), LHMDS (lithium hexamethyldisilazide) and etc. And the reaction temperature is about 0-100° C., the reaction time is 1-20 hours.

EXAMPLES

The invention is illustrated in the following nonlimiting examples in which, unless stated otherwise, room temperature or ambient temperature refer to the range of 18-25° C. Evaporation of solvent was carried out using a rotary evaporator under reduced pressure; reactions were monitored by thin layer chromatography (TLC) and reaction times were given for illustration only. Structure and purity of all isolated compounds were assured by at least one of the following techniques: TLC, mass spectrometry, nuclear magnetic resonance (NMR), high pressure liquid chromatography (HPLC). Yields are given for illustrative purpose only.

Example 1

2-(4-trifluoromethylphenyl)-3,5,7-trihydroxy-8-(3-methyl-2-buten-1-yl)-4H-chromen-4-one (compound 1)

Step 1: preparing 2-methoxy-1-(2,4,6-trihydroxyphenyl) ethanone

Phloroglucinol (35.1 g, 279 mmol) was dissolved into ethyl ether (500 mL) solution, followed by zinc chloride (8 g, 59 mmol) and 2-methoxy acetonitrile (18 g, 253 mmol) added in the solution under ice water bath condition. Dry HCl gas was bubbled into the reaction mixture, vigorously stirring for 5 hours, and precipitate was formed. The precipitate was filtered and collected, followed by dissolved into water and refluxed for 3 hours. After cooling, pink precipitate was collected, and desired white compound can be obtained after recrystallization with water. (45 g, yield 81%) $^1$HNMR (400 MHz, DMSO-d$_6$): δ=12.14 (s, 2H), 10.41 (s, 1H), 5.79 (s, 2H), 4.56 (s, 2H), 3.32 (s, 3H).

Step 2: preparation of 2-(4-trifluoromethylphenyl)-3-methoxy-5,7-dihyoxy-4H-chromen-4-one 2-methoxy-1-(2,4,6-trihydroxyphenyl) ethanone (30 g, 151 mmol) and 4-trifluomethyl benzoylchloride (37.5 g, 180 mmol) were dissolved into 250 mL dry pyridine. DUB (53.2 g 350 mmol) was dropped into the solution at room temperature. After dropping finished, the solution temperature was raised to 75° C., and kept stirring overnight. On second day, the solution was cooled to room temperature, and most solvent was removed under reduced pressure. Residue of the solution was poured into light hydrochloride solution. The mixed solution was extracted for 3 times with 500 mL ethyl acetate. The extract was combined together, washed with 300 ml 2N sodium carbonate aqueous solution, dried with anhydrous sodium sulfate and condensed. The desired compound was obtained (21 g, yield 40%) after crude product was crystallized with mixture of petroleum ether and ethyl acetate (10:1)

Step 3: preparation of 2-(4-trifluoromethylphenyl)-3,5,7-trihydroxy-4H-chromen-4-one 2-(4-trifluoromethylphenyl)-3-methoxy-5,7-dihydroxy-4H-chromen-4-one (10 g, 28.3 mmol) was dissolved into 150 mL dichloromethane in a 250 ml three-necked flask. Boron tribromide (21.2 g, 84.9 mmol) was slowly dropped into the solution at 0° C. After that, the solution was heated to room temperature and reacted for 4 hours, and quenched with 80 mL ice water for terminating the chemical reaction. The solution was extracted with 500 mL ethyl acetate for 3 times. The extracts were combined, washed with saturated sodium chloride aqueous solution once and dried with anhydrous sodium sulfate. After filtration, crude product was mixed with 20 mL ethyl acetate/petroleum (1:10) and stirred, and target yellow compound was obtained after filtering and drying. (7 g, yield 70%).

Step 4: preparation of 2-(4-trifluoromethylphenyl)-3,5,7-trihydroxy-8-(3-methyl-2-buten-1-yl)-4H-chromen-4-one (compound 1)

Compound 2-(4-trifluomethylphenyl)-3,5,7-trihydroxy-4H-chrom-4-one (3.38 g, 10 mmol) and cesium carbonate (33 g, 100 mmol) were dissolved into 100 mL water, and prenyl bromide (1.9 g, 10 mmol) was dripped into the solution under icewater bath condition. After that, the solution was kept overnight under room temperature, and pH was adjusted about 6 with 2N hydrochloride. The solution was extracted with ethyl acetate for 2 times. Organic phases were combined, washed with saturated sodium chloride aqueous solution once and dried with anhydrous sodium sulfate. After filteration, crude product was eluted with ethyl acetate/petroleum (1:25) through silica gel column. Yellow target compound (508 mg, yield 12.5%) was obtained.

$^1$H NMR (300 MHz, DMSO-d$_6$): δ=12.20 (s, 1H), 10.87 (brs, 1H), 10.07 (brs, 1H), 8.35 (d, 2H, J=8.1 Hz), 7.94 (d, 2H, J=7.7 Hz), 6.33 (s, 1H), 5.19 (t, 1H, J=5.4 Hz), 3.45 (d, 2H, J=6.0 Hz), 1.75 (s, 3H), 1.64 (s, 3H); LC-MS (ESI, m/z): 407.0 [M+H]$^-$.

Referring to the method of example 1, compound 2 to compound 8 were prepared by reacting intermediate 2-methoxy-1-(2,4,6-trihydroxyphenyl) ethanone as starting material with many different substituted alkyl chloride, aryl chloride or heteroaryl chloride, the details of the compounds are shown in the following table 1.

TABLE 1

| Compound No. | Compound name | $^1$H-NMR | LC-MS, m/z (ESI) |
|---|---|---|---|
| 2 | 2-(4-fluorophenyl)-3,5,7-trihydroxy-8-(3-methyl-2-buten-1-yl)-4H-chromen-4-one | (300 MHz, DMSO-d$_6$): δ = 12.30 (s, 1H), 10.81 (brs, 1H), 9.74 (brs, 1H), 8.21 (dd, 2H, J$_1$ = 8.7 Hz, J$_2$ = 5.7 HZ), 7.44 (dd, 2H, J$_1$ = 8.7 Hz, J$_2$ = 5.7 HZ), 6.33 (s, 1H), 5.19 (t, 1H, J = 5.4 Hz), 3.45 (d, 2H, J = 6.6 Hz), 1.76 (s, 3 H), 1.65 (s, 3 H). | 357.0 [M + H]$^+$. |
| 3 | 2-(3-fluoro-4-chlorophenyl)-3,5,7-trihydroxy-8-(3-methyl-2-buten-1-yl)-4H-chromen-4-one | (300 MHz, DMSO-d$_6$): δ = 12.16 (s, 1H), 8.06-8.00 (m, 2H), 7.82 (d, 1H, J = 8.4 Hz), 6.30 (s, 1H), 5.15 (t, 1H, J = 5.4 Hz), 3.42 (d, 2H, J = 5.7 Hz), 1.75 (s, 3H), 1.63 (s, 3H). | 391.0 [M + H]$^+$; |
| 4 | 2-(4-chlorophenyl)-3,5,7-trihydroxy-8-(3-methyl-2-buten-1-yl)-4H-chromen-4-one | (300 MHz, DMSO-d$_6$): δ = 12.25 (s, 1H), 10.83 (brs, 1H), 9.87 (brs, 1H), 8.16 (d, 2H, J = 8.7 Hz), 7.64 (d, 2H, J = 8.4 Hz), 6.31 (s, 1H), 5.17 (t, 1H, J = 5.4 Hz), 3.42 (d, 2H, J = 6.6 Hz), 1.74 (s, 3H), 1.63 (s, 3H). | 373.1 [M + H]$^+$ |
| 5 | 2-(4-trifluoromethoxyphenyl)-3,5,7-trihydroxy-8-(3-methyl-2-buten-1-yl)-4H-chromen-4-one | (300 MHz, DMSO-d$_6$): δ = 12.25 (s, 1H), 10.83 (brs, 1H), 9.93 (brs, 1H), 8.26 (d, 2H, J = 8.7 Hz), 7.58 (d, 2H, J = 8.4 Hz), 6.31 (s, 1H), 5.17 (t, 1H, J = 5.4 Hz), 3.42 (d, 2H, J = 6.6 Hz), 1.74 (s, 3H), 1.63 (s, 3H). | 423.1 [M + H]$^+$ |
| 6 | 2-(3,4-dichlorophenyl)-3,5,7-trihydroxy-8-(3-methyl-2-buten-1-yl)-4H-chromen-4-one | (300 MHz, DMSO-d$_6$): δ = 12.18 (s, 1H), 10.90 (brs, 1H), 10.15 (brs, 1H), 8.29-8.11 (m, 2H), 7.85 (d, 1H, J = 8.4 Hz), 6.32 (s, 1H), 5.15 (t, 1H, J = 5.4 Hz), 3.42 (d, 2H, J = 5.7 Hz), 1.76 (s, 3H), 1.64 (s, 3H). | 407.0 [M + H]$^+$ |
| 7 | 2-(3-trifluoromethyl-4-chlorophenyl)-3,5,7-trihydroxy-8-(3-methyl-2-buten-1-yl)-4H-chromen-4-one | (300 MHz, DMSO-d$_6$): δ = 12.16 (s, 1H), 10.76 (brs, 1H), 10.37 (brs, 1H), 8.56-8.36 (m, 2H), 7.95 (d, 1H, J = 8.4 Hz), 6.32 (s, 1H), 5.17 (t, 1H, J = 5.4 Hz), 3.41 (d, 2H, J = 5.7 Hz), 1.72 (s, 3H), 1.62 (s, 3H). | 441.0 [M + H]$^+$ |
| 8 | 2-(4-bromophenyl)-3,5,7-trihydroxy-8-(3-methyl-2-buten-1-yl)-4H-chromen-4-one | (300 MHz, DMSO-d$_6$): δ = 12.25 (s, 1H), 10.83 (brs, 1H), 9.87 (brs, 1H), 8.20 (d, 2H, J = 8.7 Hz), 7.75 (d, 2H, J = 8.4 Hz), 6.31 (s, 1H), 5.17 (t, 1H, J = 5.4 Hz), 3.42 (d, 2H, J = 6.6 Hz), 1.74 (s, 3H), 1.63 (s, 3H). | 417.2 [M + H]$^+$ |

Example 9

2-(4-trifluoromethylphenyl)-3-methoxy-5,7-dihydroxy-8-(3-methyl-2-buten-1-yl)-4H-chromen-4-one (compound 9)

Intermediate 2-(4-trifluorophenyl)-3-methoxy-5,7-dihydroxy-4H-chrom-4-one (500 mg, 1.42 mmol) of compound 1 and cesium carbonate (4.95 g, 15 mmol) were dissolved into 25 mL water, and prenyl bromide (220 mg, 1.5 mmol) was dropped into the solution under icewater bath condition. After that, the solution was kept overnight under room temperature, and pH was adjusted about 6 with 2N hydrochloride. The solution was extracted with ethyl acetate for 2 times. Organic phases were combined, washed with saturated sodium chloride aqueous solution and dried with anhydrous sodium sulfate. After filtration, crude product was eluted with ethyl acetate/petroleum through silica gel column. Yellow target compound (95 mg, yield 16.5%) was obtained.

$^1$H NMR (300 MHz, DMSO-d$_6$): δ=12.41 (1H, s), 10.92 (1H, brs), 8.20 (2H, d, J=8.1 Hz), 7.96 (2H, d, J=7.7 Hz), 6.34 (1H, s), 5.15 (1H, t, J=5.4 Hz), 3.84 (3H, s), 3.41 (2H, d, J=6.0 Hz), 1.68 (3H, s), 1.62 (3H, s); LC-MS (ESI, m/z): 421.1 [M+H]$^-$.

Example 10

2-(3,4-difluorophenyl)-3-methoxy-5,7-dihydroxy-8-(3-methyl-2-buten-1-yl)-4H-chromen-4-one (compound 10)

Step 1: preparation of 2-methoxy-1-[2,4,6-trihydroxy-3-(3-methylbut-2-ene)phenyl]ethanone Compound 2-methoxy-1-(2,4,6-trihydroxyphenyl) ethanone (2.0 g, 10.09 mmol) was dissolved into 5% potassium hydroxide (1.132 g, 20.18 mmoL) solution, followed by slowly dropping of prenyl bromide (1.504 g, 10.09 mmol) into the solution under ice water bath condition. The mixture was reacted for 2 hours under room temperature, and poured into ice water. The pH of the solution was adjusted to about 2 and extracted with ethyl acetate three times. The organic phases were combined, dried with anhydrous sodium sulfate. After filteration, crude product was purified (eluted with dichloromethane/methanol (100:1)) through silica gel column. Target compound (0.5 g, yield 18.6%) was obtained.

$^1$HNMR (400 MHz, DMSO-d$_6$): δ=13.70 (s, 1H), 10.70 (s, 1H), 10.33 (9s, 1H), 5.97 (s, 1H), 5.08 (s, 1H), 4.56 (s, 2H), 3.30 (s, 3H), 3.02 (m, 2H), 1.66 (s, 3H), 1.57 (s, 3H).

Step 2: preparing 2-(3,4-difluorophenyl)-3-methoxy-5,7-dihyoxy-8-(3-methyl-2-buten-1-yl)-4H-chromen-4-one (compound 10)

2-methoxy-1-[2,4,6-trihydroxy-3,5-di(3-methyl-2-buten-1-yl)phenyl]ethanone (250 mg, 0.94 mmol, anhydrous potassium carbonate powder (779 mg, 5.63 mmol), TBAB (tetrabutyl ammonium bromide, 454 mg, 1.41 mmol) and 3,4-difluoromethyl benzoylchloride (331 mg, 1.88 mmol) were dissolved into 30 mL toluene, refluxing for reaction for 6 hours. After cooling, toluene was removed and 20 ml water was added into the solution. The aqueous solution was extracted with ethyl acetate. Organic phases were combined, washed with saturated NaCl aqueous solution, and dried with anhydrous sodium sulfate solution, then brown residue was obtained after removing solvent. The residue was dissolved into 20 ml methanol-water (ratio 4:1) mixture, and potassium hydroxide (1 g) was added. The mixture solution was heated and refluxed for 2 hours, cooled to room temperature, acidified to pH=4 with 1N hydrochloride, and extracted with dichloromethane for three times. The combined organic phases were dried with anhydrous sodium sulfate to remove solvent. The desired compound was obtained (13.1 mg, yield 3.59%) after crude product was purified through silica gel column (eluent: ethyl acetate/petroleum ether=1:50)

$^1$H NMR (400 MHz, CDCl$_3$): δ=12.45 (s, 1H), 7.98-7.89 (m, 2H), 7.35-7.30 (m, 1H), 6.34 (s, 2H), 5.25 (br, 1H), 3.89 (s, 3H), 3.55 (d, 2H, J=6.8 Hz, 2H), 1.84 (s, 3H), 1.77 (s, 3H); LC-MS: 390.1[M+H]+; purity: 98.6% (254 nm).

Referring to the method of example 9, compound 11 to compound 13 were prepared by reacting respective corresponding intermediates as start materials with prenyl bromide through single substitution mechanism. The details of the compounds are shown as following table 2.

TABLE 2

| Compound No. | Compound name | $^1$H-NMR | LC-MS, m/z (ESI) |
|---|---|---|---|
| 11 | 2-(4-fluorophenyl)-3-methoxy-5,7-dihydroxy-8-(3-methyl-2-buten-1-yl)-4H-chromen-4-one | (300 MHz, DMSO-d$_6$): δ = 12.45 (s, 1H), 10.90 (brs, 1H), 8.13 (d, 2H, J = 8.7 Hz), 7.60 (d, 2H, J = 8.4 Hz), 6.33 (s, 1H), 5.19 (t, 1H, J = 5.4 Hz), 3.83 (s, 3H), 3.36 (d, 2H, J = 6.6 Hz), 1.61 (s, 3H). | 437.1 [M + H]$^+$. |
| 12 | 2-(3-fluoromethyl-4-chlorophenyl)-3-methoxy-5,7-dihydroxy-8-(3-methyl-2-buten-1-yl)-4H-chromen-4-one | (300 MHz, DMSO-d$_6$): δ = 12.16 (s, 1H), 10.76 (brs, 1H), 8.56-8.36 (m, 2H), 7.95 (d, 1H, J = 8.4 Hz), 6.32 (s, 1H), 5.17 (t, 1H, J = 5.4 Hz), 3.85 (s, 3H), 3.41 (d, 2H, J = 5.7 Hz), 1.72 (s, 3H), 1.62 (s, 3H). | 455.2 [M + H]$^+$; |
| 13 | 2-(4-bromophenyl)-3-methoxy-5,7-dihydroxy-8-(3-methyl-2-buten-1-yl)-4H-chromen-4-one | (300 MHz, (CD$_3$)$_2$CO): δ = 12.56 (s, 1H), 9.71 (brs, 1H), 8.16 (d, 2H, J = 8.7 Hz), 7.64 (d, 2H, J = 8.4 Hz), 6.37 (s, 1H), 5.25 (t, 1H, J = 5.4 Hz), 3.94 (s, 3H), 3.52 (d, 2H, J = 6.6 Hz), 1.77 (s, 3H), 1.66 (s, 3H). | 431.5 [M + H]$^+$ |

Test Assay for Biological Activity

Activities of the compound of formula (I) may be tested by the following assays.

Example 14

Expression of ER-α Variants in Human Breast Cancer Specimens

A membrane pre-coated with human breast cancer tissues was purchased from ProSci Incorporated (Poway, Calif.). The membrane was probed with an anti-ER-α36 antibody that specifically recognizes ER-α36 and an HRP-conjugated secondary antibody, and visualized with enhanced chemiluminescence (ECL) detection reagents (Amersham Pharmacia BiotecH). The markers on the same membrane was then eluted and detected with an anti-estrogen receptor-α antibody H222 (Novocastra Laboratories Ltd, UK) that recognizes all three subtypes of ER-α: ER-α66, ER-α46 and ER-α36. FIG. 1 shows that ER-α66, ER-α46 and ER-α36 are not expressed in normal breast tissue (Lane 1) but expressed in one specimen of infiltrating ductal carcinoma (Lane 2), one specimen of infiltrating lobular carcinoma (Lane 5) and non-invasive ductal carcinoma (Lane 7). In addition, ER-α36 was expressed in invasive ductal carcinoma (Lane 4) and another specimen of infiltrating lobular carcinoma (Lane 6). Lane 2 and 3 had infiltrating ductal carcinoma respectively from two different patients. Lanes 5 and 6 had infiltrating lobular carcinoma from two different patients, respectively. This result indicates that ER-α36 is not expressed in normal breast tissue but expressed in ER-negative breast cancer samples that do not express ER-α66 and ER-α46.

Example 15

ER-α36 expressed in the ER-negative Breast Cancer Cell Line, MDA-MB-231

Figure 2:
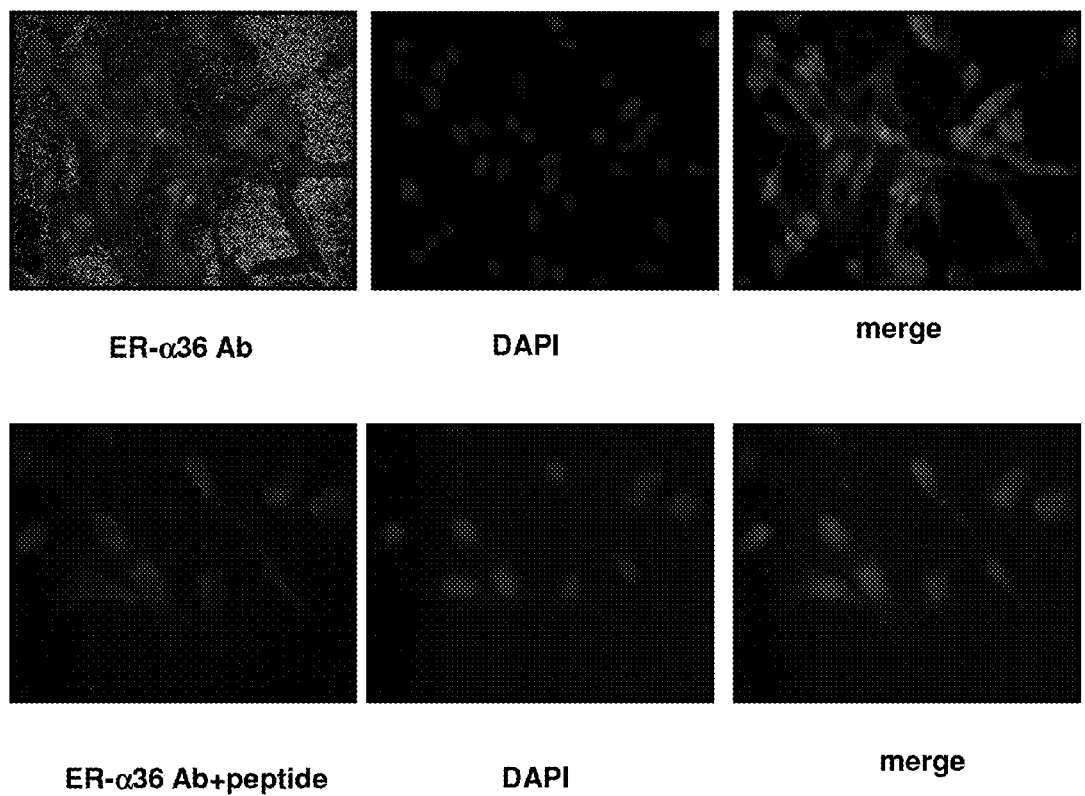
FIG. 2 (upper figure) shows immunofluorescence staining result of MDA-MB-231 cells. The MDA-MB-231 cells are ER-negative breast cancer cell line that lacks ER-α66 and ER-α46, stained with an antibody that specifically binds to ER-α36 (shown in the left figure labeled with "ER-α36 Ab": positive shown in green). Cell nucleus is also stained with 4,6-diamidine-2-phenylidole (shown in the middle figure labeled with "DAPI": positive staining shown in blue). Merged staining signals are shown in a lane labeled with "Merge". Negative staining is observed when the antibody is preincubated with immunogen peptides that binds to the antibody (lower figure).

The MDA-MB-231 cell line is well-known for lacking ER-α66 and ER-α46 (Relevance of breast cancer cell lines as models for breast tumors: an update. Marc Lacroix, Guy Leclercq, Breast Cancer Research and Treatment 83: 249-289 (2004)). MDA-MB-231 cells were obtained from American Type Culture Collection (ATCC). MDA-MB-231 cells were grown on 8-well BIOCOAT chamber slides (BD Science Discovery Labware) in a 8% $CO_2$ atmosphere in Dulbecco's Modified Eagle's Medium (DMEM) and 10% fetal calf serum at 37° C. for 12 hours. Then the cells were washed twice with sterile Phosphate Buffered Saline (PBS) and fixed with 4% paraformaldehyde in PBS (pH7.4) for 30 minutes at room temperature. After that, the cells were washed with PBS, permeabilized with 0.5% (v/v) Triton X-100 for 10 minutes. The cells were then washed with PBS again, and blocked with 3% serum in PBS at room temperature for 1 hour. The slides were incubated with an ER-α36 specific antibody or the same antibody preincubated with immunogen peptides that specifically bind to the ER-α36 antibody for 30 minutes at room temperature for 1 hour and washed three times with PBS containing 0.5% Triton X-100 (PBST), then incubated with a fluorescein isothiocyanate (FITC)-labelled secondary antibody. Finally, the slides were washed three times with PBST, one time with PBS, then coated with immunofluorescent label (Molecular Probes, Eugene, Oreg.) and examined under a Nikon E600 Microscope and images were captured by MRC-1024 confocal imaging system (Bio-Rad). FIG. 2 (upper panel) shows that MDA-MB-231 cells were positively stained by an anti-ER-α36 antibody. In order to prove reliability of this result, the image with the same anti-ER-α36 antibody preincubated with immunogen peptides did not show any stain (FIG. 2, lower panel), indicating the specificity of the antibody.

Example 16

Expression of ER-α36 in Different Tumor Cell Lines by Western Blot

Figure 3:
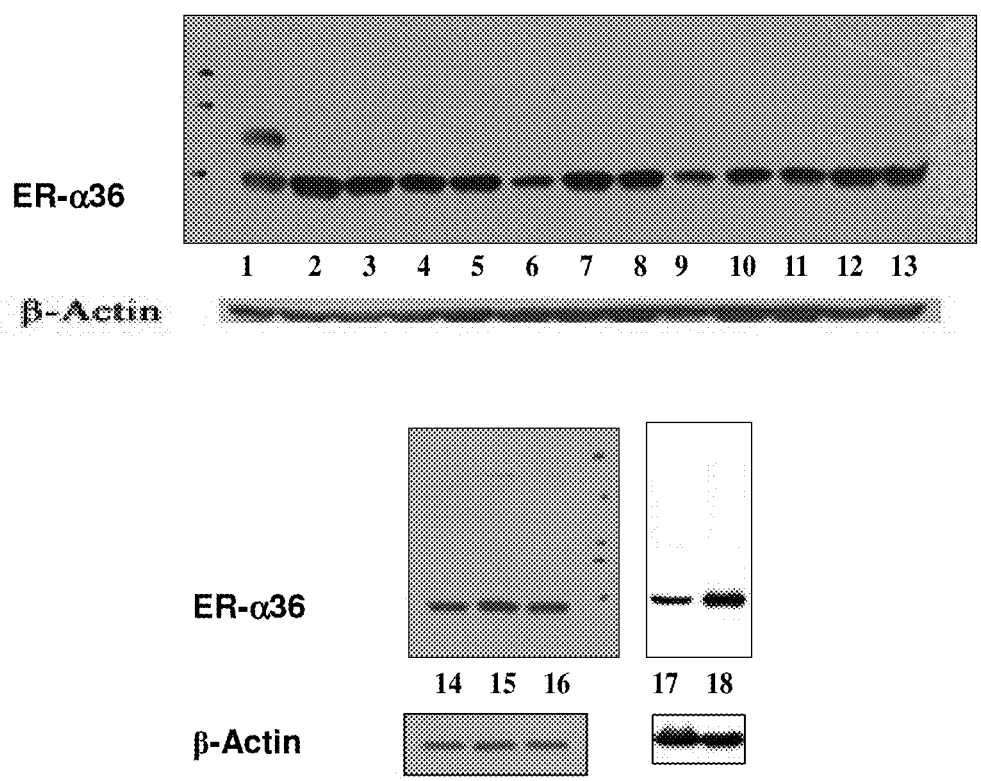
FIG. 3 shows Western blot results depicting the expression of ER-α36 in different tumor cell lines. Lane 1: 293 human renal epithelial cell lines that have transient expression of ER-α36; Lane 2-4: cell lines SK-BR-3 of human breast cancer from different labs; Lane 5-7: cell lines MCF-7 of human breast cancer from different labs; Lane 8-9: cell lines HL-60 of human leukemia from different labs; Lane 10-11: cell lines MV-4-11 of human leukemia from different labs; Lane 12-13: cell lines K562 of human chronic myeloid leukemia from different labs; Lane 14: cell line A2780 of liver cancer; Lane 15: cell line HEL-7402 of liver cancer; Lane 16: cell line HEL-9204 of liver cancer; Lane 17: primary cell line Hep-11 of liver cancer from a patient; Lane 18: primary cell line Hep-12 of liver cancer from a patient.

The sample cells were cultured at 37° C., 5% $CO_2$ (MDA-MB-231, and the culture medium is 10% FBS-DMEM). The cells was collected till the cells in each well reached 60-90% confluence and centrifugated for 5 minutes at 4° C., 4300 rpm. Supernatant of the solution was removed, and proper lysate, Lysis buffer comprising 1% NP-40 and 0.7 mM EDTA, and protease inhibitor were added, the cells in the solution were kept lysising for 30 minutes to 1 hour in ice bath. The solution was centrifugated for 15 minutes at 14000 rpm and the supernatant was collected to be quantified with protein. General procedure of western blot was shown as follows: transmembrane on prefabricated glue or mixed glue, electrophoresis, blocking anti-ER-α36 antibody, elution, blocking secondary antibody, elution, expressing exposure in the photographic laboratory and showing results. FIG. 3 shows Western blot result of Expression of ER-α in different tumor cells.

Lane 1: 293 human renal epithelial cell lines of transient expression of ER-α36; Lane 2-4: cell lines SK-BR-3 of human breast cancer from different labs; Lane 5-7: cell lines MCF-7 of human breast cancer from different labs; Lane 8-9: cell lines HL-60 of human leukemia from different labs; Lane 10-11: cell lines MV-4-11 of human leukemia from different labs; Lane 12-13: cell lines K562 of human chronic myeloid leukemia from different labs; Lane 14: cell line A2780 of liver cancer; Lane 15: cell line HEL-7402 of liver cancer; Lane 16: cell cancer HEL-9204 of liver cancer; Lane 17: primary cell line Hep-11 of liver cancer from a patient; Lane 18: primary cell line Hep-12 of liver cancer from a patient.

Example 17

The Compound Inhibiting In Vitro Growth of Different Breast Cancer Cells

A: CellTiter-Glo® Luminescent Cell Viability Assay on ER-Negative Breast Cancer MDA-MB-231 In Vitro:

MDA-MB-231 cells were maintained at 37° C., in a 5% $CO_2$ atmosphere in DMEM and 10% fetal calf serum. The cells were placed at a density of $6\times10^3$ cells per well in a 96-well plate. MDA-MB-231 cells were treated with a test compound dissolved in DMSO at the concentration of 0, 0.3 μM, 0.5 μM, 1 μM, 2 μM, 3 μM, 5 μM, 10 μM, 20 μM, 30 μM, 50 μM and 100 μM for 72 hours. Treated cells were examined under CellTiter-Glo® Luminescent Cell Viability Assay Kit (Promega), and luminescence were recorded with Envision.

B: CellTiter-Glo® Luminescent Cell Viability Assay on ER-Positive Breast Cancer MCF-7 Cells In Vitro:

MCF7 cell line is a breast cancer cell line that strongly expresses ER-66, ER-46 and ER-36 (Relevance of breast cancer cell lines as models for breast tumours: an update. Marc Lacroix, Guy Leclercq, Breast Cancer Research and Treatment (2004) 83, 249-289; Wang et al., Proc. Natl. Acad. Sci. U.S.A. 103: 9063-9068 (2006)). MCF7 cells from ATCC were maintained in an Dulbecco's modified Eagle medium (DMEM), and 10% fetal calf serum at 37 in a 5% $CO_2$ atmosphere. Cells were placed at a density of $6\times10^3$ cells per well in a 96-well plate. MCF 7 cells were treated with a test compound dissolved in DMSO at the concentration of 0, 0.3 μM, 0.5 μM, 1 μM, 2 μM, 3 μM, 5 μM, 10 μM, 20 μM, 30 μM, 50 μM and 100 μM for 72 hours. Treated cells were examined through CellTiter-Glo® Luminescent Cell Viability Assay Kit (Promega), and luminescence were recorded with Envision.

Table 3 shows the viability of different breast cancer cells influenced by some compounds of the present invention.

TABLE 3

| | Inhibition of viability of breast cancer cells IC$_{50}$ (μM) | |
|---|---|---|
| Compound No. | MDA-MB-231 cells | MCF7 cells |
| Tamoxifen [a) | 20.90 ± 1.51[b) | 22.55 ± 4.15 |
| 1 | 1.066 | 2.012 |
| 2 | NA [c) | 3.167 |
| 3 | 2.867 | 8.603 |
| 4 | 4.325 | 16.011 |
| 5 | 4.476 | 6.854 |
| 6 | 1.875 | 6.854 |
| 7 | 9.303 | 7.542 |
| 9 | NA | NA |
| 10 | NA | 31.46 |

[a) tamoxifen as positive control compound.
[b) when the compound was tested more than 3 times, IC$_{50}$ was illustrated with average value ± standard deviation.
[c) NA means no activity, and IC$_{50}$ was above 100 μM
d): ND means not being detected.

Example 18

Inhibition of Growth of Chronic Leukemia Cells In Vitro by the Compounds

A: Detection of Viability of Chronic Leukemia Cells K562 by CellTiter-Glo® Luminescent Assay In Vitro The chronic leukemia cells K562 from ATCC were maintained in IMDM and 10% fetal calf serum at 37° C. in a 5% $CO_2$ atmosphere. The cells were subseeded in a 96-well culture plate at a cencentration of 6×10$^3$ cells/well.K562 cells were treated with a test compound dissolved in DMSO at the concentration of 0, 0.3 μM, 0.5 μM, 1 μM, 2 μM, 3 μM, 5 μM, 10 μM, 20 μM, 30 μM, 50 μM and 100 μM for 72 hours. Treated cells were examined by CellTiter-Glo® Luminescent Cell Viability Assay Kit (Promega), and luminescence were recorded with Envision.

Example 19

Inhibition of Growth of Human B Lymphoma Daudi Cells In Vitro by the Compounds A: Inhibition of Human B Lymphoma Daudi Cells by CellTiter-Glo® Luminescent Assay In Vitro The Human B Lymphoma Daudi cells from ATCC were maintained in IMDM and 10% fetal calf serum at 37° C. in a 5% $CO_2$ atmosphere. The cells were subseeded in a 96-well culture plate at a concentration of 6×10$^3$ cells/well. Human B Lymphoma Daudi cells were treated with a test compound dissolved in DMSO at the concentration of 0, 0.3 μM, 0.5 μM, 1 μM, 2 μM, 3 μM, 10 μM, 20 μM, 30 μM, 50 μM and 100 μM for 72 hours. Treated cells were examined by CeliTiter-Glo® Luminescent Cell Viability Assay Kit (Promega), and luminescence were recorded with Envision.

Table 4 shows the viability of chronic leukemia cells K562 and Human B Lymphoma Daudi cells influenced by some compounds of the present invention.

TABLE 4

| | Inhibition of viability of cells in vitro IC$_{50}$ (μM) | |
|---|---|---|
| Compound No. | K562 cells | Daudi cells |
| Gleevec[a) | 0.751 | ND[b) |
| cytarabinen | ND | 10.033 |

TABLE 4-continued

| | Inhibition of viability of cells in vitro IC$_{50}$ (μM) | |
|---|---|---|
| Compound No. | K562 cells | Daudi cells |
| 1 | 1.035 | 0.824 |
| 2 | 6.139 | 9.234 |
| 3 | 1.849 | 2.909 |
| 4 | 0.974 | 2.638 |
| 5 | 1.475 | 1.486 |
| 6 | 0.935 | 1.983 |
| 7 | 6.140 | 4.068 |
| 10 | NA | 21.75 |
| 11 | NA | NA |

[a): gleevec and cytarabinen respectively were positive control compound for K562 cells model and Daudi cells model
[b): Nd means no detection
c) NA means no activity, and IC$_{50}$ was above 100 μM

Example 20

Inhibition of Growth of Acute Leukemia Cells In Vitro by the Compounds

A: Inhibition of Growth of Acute Myeloblastic Leukemia HL-60 Cells by the Compounds Detected by MTT Method The acute myeloblastic leukemia HL-60 cells from ATCC were maintained in IMDM and 10% fetal calf serum at 37° C. in a 5% $CO_2$ atmosphere. The cells were subseeded in a 96-well culture plate at a concentration of 6×10$^3$ cells/well. HL-60 cells were treated with a test compound dissolved in DMSO at the concentration of 0, 10$^{-4}$M, 10$^{-5}$M, 10$^{-6}$M, 10$^{-7}$M, 10$^{-8}$M for 72 hours. OD value was tested by MTT method, and the inhibition ratio was calculated.

B: Inhibition of Growth of Acute Lymphoblastic Leukemia Molt-4 Cells by the Compounds Detected by MTT Method The acute lymphoblastic leukemia Molt-4 cells from ATCC were maintained in RPMI-1640 and 10% fetal calf serum at 37° C. in a 5% $CO_2$ atmosphere. The cells were subseeded in a 96-well culture plate at a concentration of 6×10$^3$ cells/well and maintained RPMI-1640 and 10% fetal calf serum at 37° C. 5%$CO_2$ atmosphere. Molt-4 cells were treated with a test compound dissolved in DMSO at the concentration of 0, 10$^{-4}$M, 10$^{-5}$M, 10$^{-6}$M, 10$^{-7}$M, 10$^{-8}$M for 72 hours. OD value was tested by MTT method, and the inhibition ratio was calculated.

The viability of different leukemia cells influenced by some compounds of the invention was listed in following table 5

TABLE 5

| | The inhibition percentage of cell proliferation by the compounds with a concentration of 10$^{-6}$M (%) | |
|---|---|---|
| Compound No. | HL-60 cells | Molt-4 cells |
| Doxorubicin[a) | 79.0 | 90.1 |
| 1 | 60.7 | 43.7 |
| 2 | Na[b) | NA |
| 3 | 28.5 | 14.4 |
| 4 | 0.974 | 14.7 |
| 5 | 59.8 | 69.4 |
| 6 | 61.9 | 67.4 |
| 7 | NA | 57.0 |

TABLE 5-continued

| Compound No. | The inhibition percentage of cell proliferation by the compounds with a concentration of $10^{-6}$M (%) | |
| --- | --- | --- |
| | HL-60 cells | Molt-4 cells |
| 9 | NA | NA |
| 11 | NA | NA |

[a]: Doxorubicin as positive control compound
[b]: NA means no activity, and inhibition percentage by the compound with a concentration of $10^{-6}$M was below 10%.

Example 21

The Inhibition of Liver Cancer Cells In Vitro by the Compounds

A: Inhibition of Liver Cancer Cell BEL-7402 In Vitro by the Compounds Detected by SRB The liver cancer BEL-7402 cells from ATCC were maintained in DMDM, 10% NCS and 50 μg/ml KANA at 37° C. in a 5% $CO_2$ atmosphere, and were subseeded in a 96-well culture plate at a concentration of $6\times10^3$ cells/well. BEL-7402 cells were treated with a test compound dissolved in DMSO at the concentration of 0, $10^{-4}$M, $10^{-5}$M, $10^{-6}$M, $10^{-7}$M, $10^{-8}$M for 72 hours. OD value was tested by SRB method, and the inhibition percentage was calculated.

The inhibition of liver cancer cells by some compounds of the invention was listed in following Table 6

TABLE 6

| Compound No. | The inhibition percentage of cell proliferation by the compounds with a concentration of $10^{-6}$M (%) BEL-7402 cells |
| --- | --- |
| Doxorubicin[a] | 55.2 |
| 1 | 23.7 |
| 2 | 21.8 |
| 3 | 28.6 |
| 4 | 46.4 |
| 5 | 15.6 |
| 6 | 14.9 |
| 7 | 19.8 |
| 9 | 11.7 |
| 10 | 17.4 |

[a]: Doxorubicin as positive control compound

Example 22

The Inhibition of Gastric Cancer Cells In Vitro by the Compounds

Figure 4:
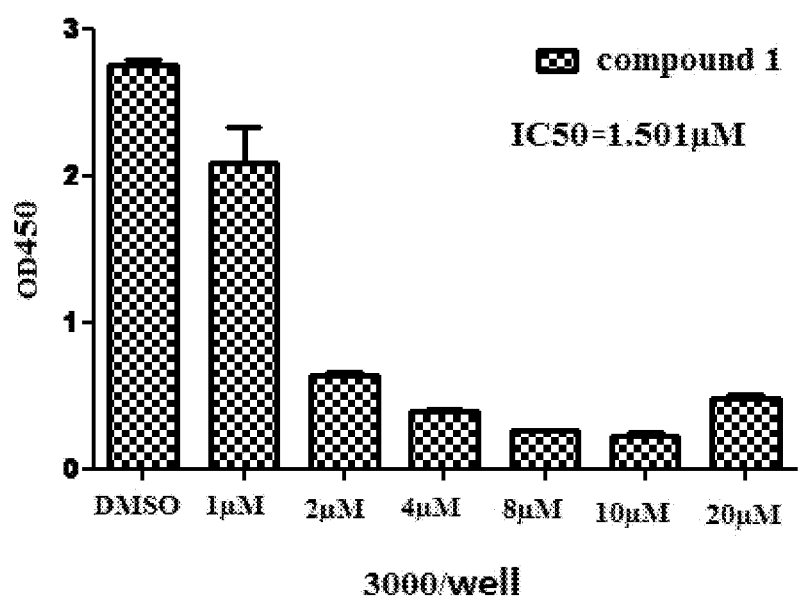
FIG. 4-8 shows in vitro inhibition on cell line BGC-823 of gastric cancer, cell line H460 of lung cancer, cell line LS174T of colon carcinoma, cell line PANC-1 of pancreatic cancer and cell line PC-3 of prostatic cancer with compound 1, tested by MTT method. The results show compound 1 has dominant inhibition on these cancer cells with good dosage dependency. IC50 is in the range of 1-4 μM.

A: Inhibition of Gastric Cancer Cell BGC-823 In Vitro by the Compounds by MTT Method The gastric cancer BGC-823 cells were subseeded in a 96-well culture plate at a concentration of $3\times10^3$ cells/well and maintained in phenol red free DMEM medium containing 2.5% CS-FBS at 37° C. in a 5% $CO_2$ atmosphere. BGC-823 cells were treated with a test compound dissolved in DMSO at the concentration of 0, 1, 2, 4, 8, 10 and 20 μM for 72 hours. OD value was tested by MTT method, and the inhibition percentage was calculated. The result is shown in FIG. 4.

Example 23

The Inhibition of Lung Cancer Cells In Vitro by the Compounds

A: Inhibition of Lung Cancer Cells H460 In Vitro by the Compounds by MTT Method

Figure 5:
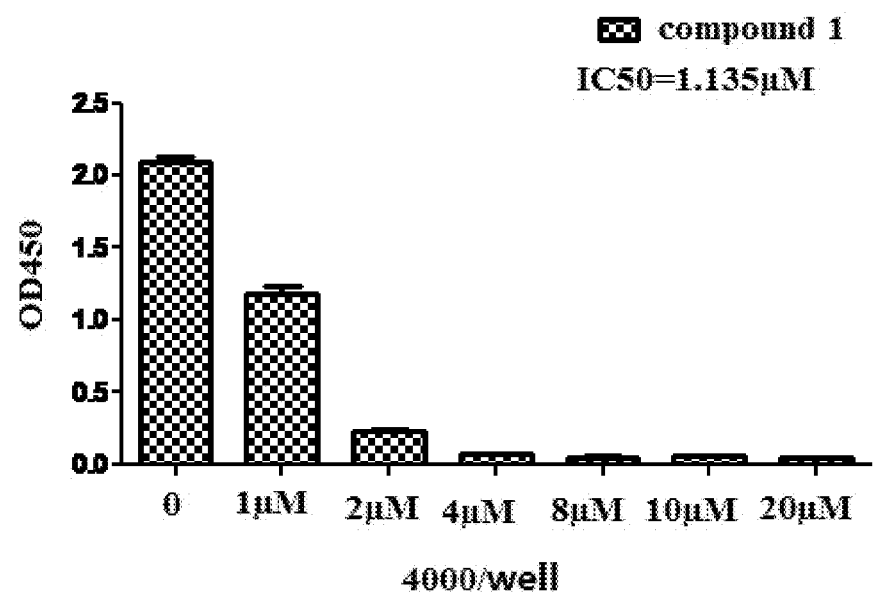

The lung cancer H460 cells were subseeded in a 96-well culture plate at a concentration of $4.0\times10^3$ cells/well and maintained in phenol red free medium containing 2.5% CS-FBS at 37° C. in a 5% $CO_2$ atmosphere. H460 cells were treated with a test compound dissolved in DMSO at the concentration of 0, 1, 2, 4, 8, 10 and 20 μM for 72 hours. OD value was tested by MTT method, and the inhibition percentage was calculated. The result is shown in FIG. 5.

Example 24

The inhibition of colon cancer cells in vitro by the compounds

Figure 6:
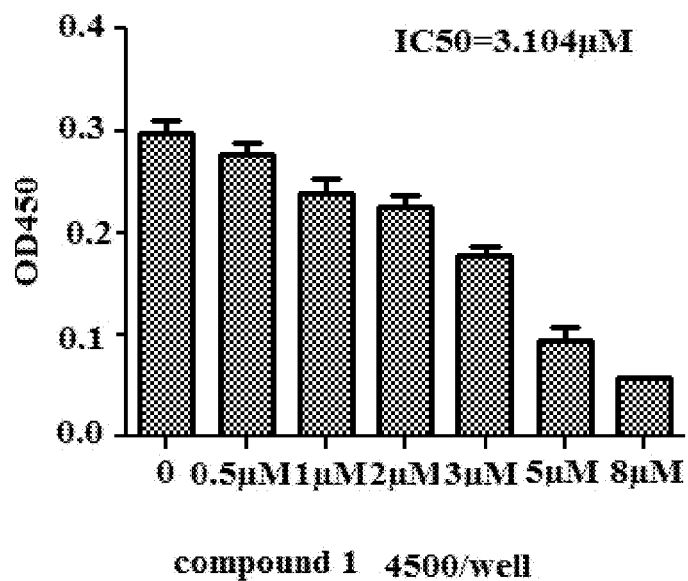

A: Inhibition of Colon Cancer Cells LS174T In Vitro by the Compounds by MTT Method The colon cancer LS174T cells were subseeded in a 96-well culture plate at a concentration of $4.5\times10^3$ cells/well and maintained in phenol red free 1640 medium containing 2.5% CS-FBS at 37° C. in a 5% $CO_2$ atmosphere. LS174T cells were treated with a test compound dissolved in DMSO at the concentration of 0, 1, 2, 4, 8, 10 and 20 μM for 72 hours. OD value was tested by MTT method, and the inhibition percentage was calculated. The result is shown in FIG. 6.

Example 25

The Inhibition of Pancreatic Cancer Cells In Vitro by the Compounds

Figure 7:
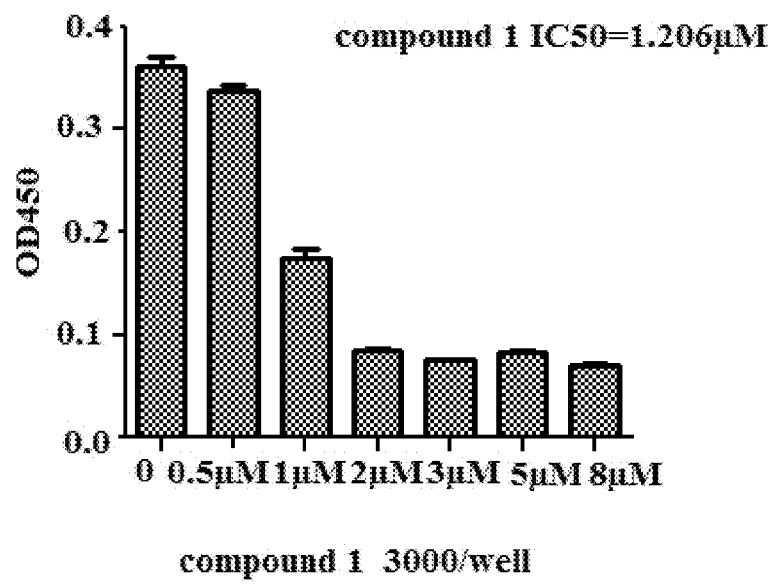

A: Inhibition of Pancreatic Cancer Cells PANC-1 In Vitro by the Compounds by MTT Method The pancreatic cancer PANC-1 cells were subseeded in a 96-well culture plate at a concentration of $3\times10^3$ cells/well and maintained in phenol red free 1640 medium containing 2.5% CS-FBS at 37° C. in a 5% $CO_2$ atmosphere. PANC-1 cells were treated with a test compound dissolved in DMSO at the concentration of 0, 1, 2, 4, 8, 10 and 20 μM for 72 hours. OD value was tested by MTT method, and the inhibition percentage was calculated. The result is shown in FIG. 7.

Example 26

The Inhibition on Prostate Cancer Cells In Vitro by the Compounds

Figure 8:
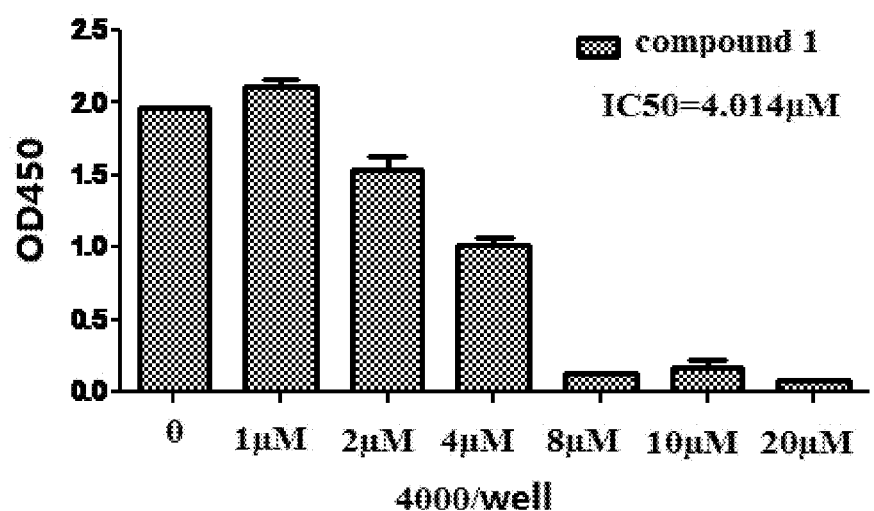

A: Inhibition of Prostate Cancer Cells PC-3 In Vitro by the Compounds by MTT Method The pancreatic cancer PC-3 cells were subseeded in a 96-well culture plate at a concentration of $3\times10^3$ cells/well and maintained in medium containing 10% F12K fetal bovine serum. PC-3 cells were treated with the test compound dissolved in DMSO at the concentration of 0, 1, 2, 4, 8, 10 and 20

μM for 72 hours. OD value was tested by MTT method, and the inhibition percentage was calculated. The result is shown in FIG. 8.

In Vivo Assay:

Example 27

Figure 9:
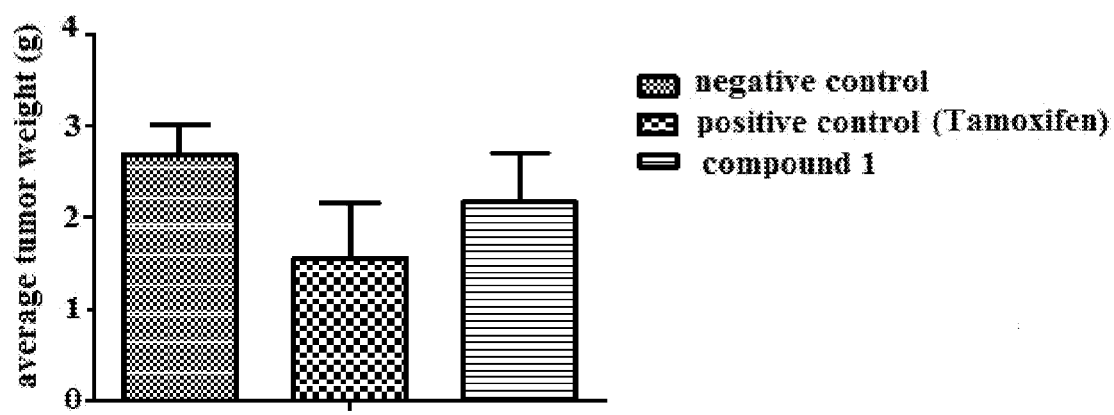
FIG. 9 shows average tumor weight (bar a) of human breast cancer BCAP-37 tumor bearing nude mice after 20 days of continuous administration respectively with positive control of tamoxifen (0.7 mg/mouse/day), compound 1 (0.7 mg/mouse/day) and negative control of vehicle (0.2 mg/mouse/day), and the result shows inhibition of compound on the tumors.

Inhibition of Growth of Human Breast Cancer BCAP-37 Cells Xenograft Tumor in Nude Mice by the Compounds Nude mice with breast cancer xenografts were treated with the test compounds to test their effect on inhibiting tumor growth. Tumor tissues were taken from nude mice bearing BCAP-37 breast cancer and cut into small pieces. Several pieces of the tumor tissues were implanted into the armpit under the right front limb of female nude mice. After the implantation, the mice are fed with E2β solution once a day at the dosage of 7 μg per mouse for 6 days to stimulate growth of tumor in the experiment mice. Starting on the seventh day, the mice were intragastric administered with the test solution containing the compounds and corn oil at the dosage of 35 mg/kg. Tamoxifen was used as a positive control. Corn oil was used as a negative control. The test solution was prepared by dispersing test compound in corn oil solution. (20 mg/mL). The mice were given the test solution and Tamoxifen at the dosage of 35 mg/kg or corn oil once a day for 15 days. Then the mice were sacrificed and the tumor tissues were dissected and weighed. The tumor growth inhibition rate was a percentage calculated using the formula: tumor growth inhibition rate=(average weight of the tumor in the negative control−average weight of the tumor treated with test compound)/average weight of the tumor in the negative control. The result is drawn as bar graph and listed in FIG. 9.

Example 28

Figure 10:
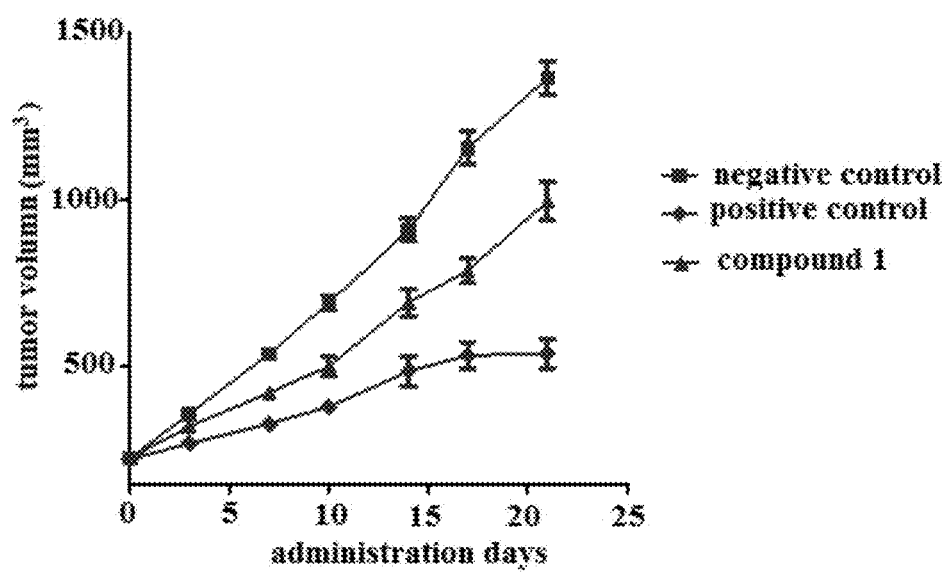
FIG. 10 shows tumor growth curve of human B lymphoma Daudi cells bearing nude mice being continuously administered respectively with positive control of rituximab, compound 1 (0.7 mg/mouse/day) and negative control of vehicle (0.2 mL/mouse/day) for 21 days.

Inhibition of Growth of Human B Cell Lymphomas Daudi Xenograft Tumor in Nude Mice by the Compounds Nude mice with Human B cell Lymphomas Daudi Xenograft Tumor were treated with the test compounds to test their effect on inhibiting tumor growth. Human B cell Lymphomas were from ATCC. $1 \times 10^7$ cells with 0.2 mL Matrigel after 5 passages were implanted into the armpit under the right front limb of female nude mice. When the tumor of the nude mice reached 150-200 mm$^3$, the tumor-bearing nude mice were grouped randomly. Every 10 nude mice belong to one group. The intragastric administration with the mixed oil was as negative control and intravenous administration with rituximab was as positive control. The test compound was dissolved in the mixed oil. The administration period was 21 days continuously, and the mixed oil suspension (35 mg/kg) with test compound was administered on the nude mice of the positive group once a day. The Rituximab (20 mg/kg) was injected to the positive control twice a week. The negative group with the mixed oil was intragastrically administered every day. During the administering period, the tumor volume and nude mice weight were measured twice a week. Drawing tumor growth figure based on tumor volume and administering time (FIG. 10), thereby the effect of the compound on the growth of tumor could be estimated.

Example 29

Figure 11:
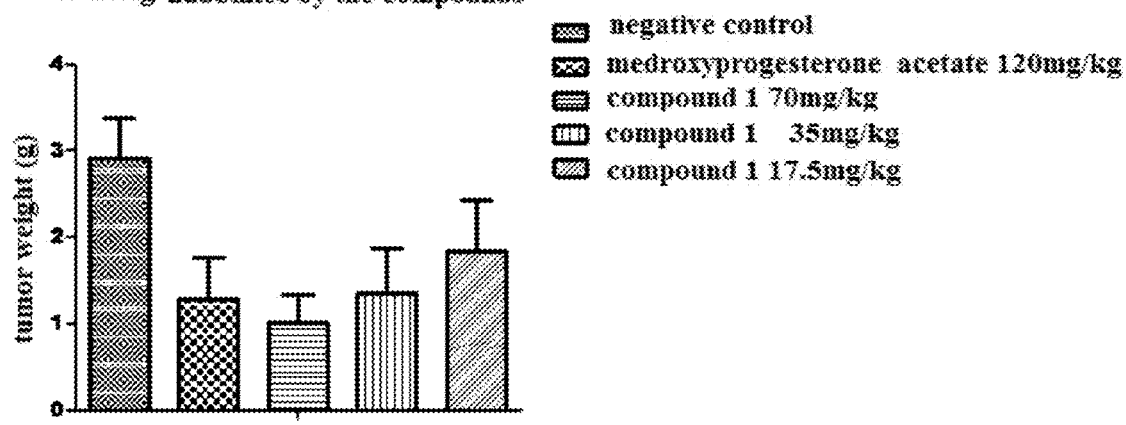
FIG. 11 shows average tumor weight of human endometrial carcinoma Ishikawa bearing nude mice after 20 days of continuous administration respectively with positive control of DMPA (depomedroxy progesterone acetate) (120 mg/kg), compound 1 of low dosage (17.5 mg/kg), middle dosage (35 mg/kg), high dosage (70 mg/kg) and negative control of vehicle (0.2 mL/mouse/day). Compound 1 has dominant inhibition on tumor growth of tumor bearing mice, and the inhibition effect is higher than control drug.

Inhibition of Growth of Human Endometrial Cancer Ishikawa Cells Xenografts by the Compounds Nude mice with Human endometrial cancer Ishikawa cells Xenograft Tumor were treated with the test compounds to test their effect on inhibiting tumor growth. Tumor was taken from nude mice with Ishikawa cells and cut into small pieces. Small pieces of tumor were implanted into the armpit under the right front limb of female nude mice. After the implantation, the mice were injected with E2β solution once a day at the dosage of 7 μg per mouse for 6 days to stimulate growth in the expriment mice. Starting on the seventh day, the mice were intragastric administered with a solution containing the test compounds and corn oil at the dosage of 35mg/kg. Medroxyprogesterone acetate was used as a positive control. Mixed oil was used as a negative control. The test compound was dispersed in mixed oil (20 mg/mL). The mice were respectively administered the test compound, Medroxyprogesterone acetate and mixed oil at the dosage of 35 mg/kg for 15-21 days. Then the mice were sacrificed and the tumor tissues were dissected and weighed. The tumor growth inhibition rate was a percentage calculated using the formula: tumor growth inhibition rate=(average weight of the tumor in the negative control—average weight of the tumor treated with test compound) / average weight of the tumor in the negative control. The result is drawn as bar graph, referring to FIG. 11.

We claims:

1. A compound of formula (I) or pharmaceutically acceptable salt thereof,

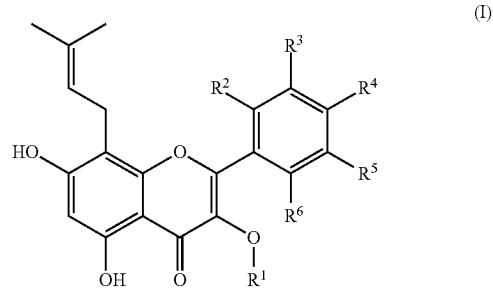

wherein:
R$^1$ is selected from the group consisting of hydrogen, (C$_{1-6}$) alkyl, and (C$_{1-6}$) alkyl substituted with one or more halogen atoms;
R$^2$, R$^3$, R$^5$ and R$^6$ are independently selected from the group consisting of hydrogen, (C$_{1-4}$) alkyl, (C$_{1-4}$) alkyl substituted with one or more halogen atoms, halogen, cyano and (C$_{1-4}$) alkoxy substituted with one or more halogen atoms, and R$^4$ is methyl or methyl substituted with one or more halogen atoms.

2. The compound of formula (I) of claim 1, or pharmaceutically acceptable salt thereof,

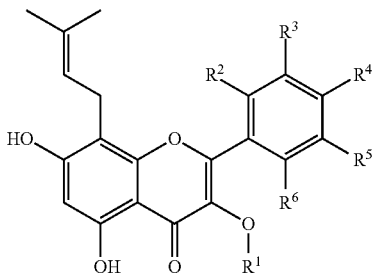
(I)

wherein R¹ is selected from the group consisting of hydrogen, methyl, ethyl, trifluoromethyl, and difluoromethyl; R², R³, R⁵ and R⁶ are independently selected from the group consisting of hydrogen, methyl, ethyl, propyl, isopropyl, butyl, halogen, cyano, ($C_{1-4}$) alkyl substituted with one or more halogen atoms, and ($C_{1-4}$) alkoxy substituted with one or more halogen atoms; and R⁴ is methyl or methyl substituted with one or more halogen atoms.

3. The compound of claim 2, when R¹ is hydrogen, having the structure according to formula (II)

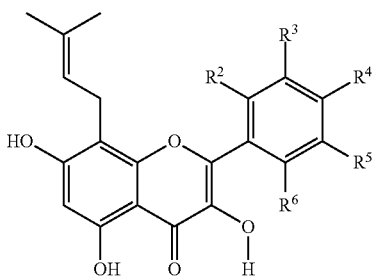
(II)

wherein,
R², R³, R⁵ and R⁶ are independently selected from the group consisting of hydrogen, methyl, ethyl, propyl, isopropyl, butyl, halogen, cyano, ($C_{1-4}$) alkyl substituted with one or more halogen atoms, and ($C_{1-4}$) alkoxy substituted with one or more halogen atoms; and R⁴ is methyl or methyl substituted with one or more halogen atoms.

4. The compound of the claim 2, when R¹ is methyl, having the structure according to formula (III)

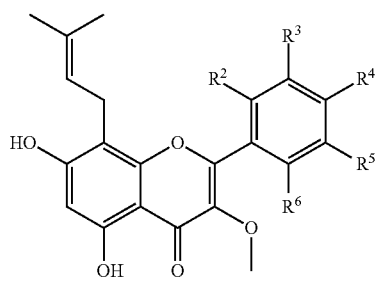
(III)

wherein,
R², R³, R⁴, R⁵ and R⁶ are independently selected from the group consisting of hydrogen, methyl, ethyl, propyl, isopropyl, butyl, halogen, cyano, ($C_{1-4}$) alkyl substituted with one or more halogen atoms, and ($C_{1-4}$) alkoxy substituted with one or more halogen atoms; and R⁴ is methyl or methyl substituted with one or more halogen atoms.

5. The compound of claim 1, selected from the group consisting of:
2-(4-trifluoromethylphenyl)-3,5,7-trihydroxy-8-(3-methyl-2-buten-1-yl)-4H-chromen-4-one; and
2-(4-trifluoromethylphenyl)-3-methoxy-5,7-dihydroxy-8-(3-methyl-2-buten-1-yl)-4H-chromen-4-one.

6. A pharmaceutical composition comprising a therapeutically effective amount of the compound according to claim 1 or pharmaceutically acceptable salt thereof, in combination with one or more pharmaceutically acceptable excipients.

7. A method of treating a cancer related to ER-α36 in a patient in need thereof comprising administering to said patient a therapeutically effective amount of the compound of claim 1, or pharmaceutically acceptable salt thereof, wherein said cancer is selected from breast cancer, renal cancer, acute myeloblastic leukemia, acute lymophoblastic leukemia, human chronic myeloid leukemia, liver cancer, gastric cancer, colon cancer, lung cancer, endometrial cancer, prostate cancer, pancreatic cancer, and lymphoma cancer.

8. The method of claim 7, wherein the cancer is breast cancer.

* * * * *

UNITED STATES PATENT AND TRADEMARK OFFICE
CERTIFICATE OF CORRECTION

PATENT NO. : 9,221,781 B2  
APPLICATION NO. : 14/371866  
DATED : December 29, 2015  
INVENTOR(S) : Meng et al.

Page 1 of 1

It is certified that error appears in the above-identified patent and that said Letters Patent is hereby corrected as shown below:

Title page, It Should Read:

(73) Assignee: BEIJING SHENOGEN PHARMA GROUP LTD., Beijing (CN)

Signed and Sealed this
Twenty-sixth Day of July, 2016

Michelle K. Lee
*Director of the United States Patent and Trademark Office*